United States Patent
Gong et al.

(10) Patent No.: US 12,377,052 B2
(45) Date of Patent: Aug. 5, 2025

(54) DUAL-RESPONSIVE NANOPARTICLES FOR ENHANCED ANTIBACTERIAL EFFICACY

(71) Applicant: Wisconsin Alumni Research Foundation, Madison, WI (US)

(72) Inventors: Shaoqin Gong, Middleton, WI (US); Mingzhou Ye, Madison, WI (US); David R. Andes, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 712 days.

(21) Appl. No.: 17/506,614

(22) Filed: Oct. 20, 2021

(65) Prior Publication Data

US 2022/0117904 A1 Apr. 21, 2022

Related U.S. Application Data

(60) Provisional application No. 63/094,783, filed on Oct. 21, 2020.

(51) Int. Cl.
| | | |
|---|---|---|
| *A61K 9/51* | (2006.01) | |
| *A61K 9/50* | (2006.01) | |
| *A61K 31/496* | (2006.01) | |
| *A61P 31/04* | (2006.01) | |
| *B82Y 5/00* | (2011.01) | |
| *C08G 63/688* | (2006.01) | |

(52) U.S. Cl.
CPC .......... *A61K 9/5153* (2013.01); *A61K 9/5036* (2013.01); *A61K 31/496* (2013.01); *A61P 31/04* (2018.01); *B82Y 5/00* (2013.01); *C08G 63/688* (2013.01)

(58) Field of Classification Search
None
See application file for complete search history.

(56) References Cited

PUBLICATIONS

Chemical Abstract Registry No. 36837-96-4, indexed in the Registry File on STN CAS Online Nov. 16, 1984.*

Brandis, et al., "Fitness-compensatory mutations in rifampicin-resistant RNA polymerase," Molecular Microbiology, 85(1):142-151 (2012).
Chung, et al., "Antimicrobial peptides as potential anti-biofilm agents against multidrug-resistant bacteria," Journal of Microbiology, Immunology and Infection, 50(4):405-410 (2017).
Clinical Institute LS, "Methods for dilution antimicrobial susceptibility tests for bacteria that grow aerobically; approved standard-ninth edition," Clinical and Laboratory Standards Institute, Wayne, PA, M07-A9, 32(2):88 pages, Jan. 2012.
Lawrence, et al., "Determination of diffusion coefficients in biofilms by confocal laser microscopy," Applied and Environmental Microbiology, 60(4):1166-1173 (1994).
Lehar, et al., "Novel antibody—antibiotic conjugate eliminates intracellular *S. aureus*," Nature, 527(7578):323 (2015).
Muller, et al., "The determination and interpretation of the therapeutic index in drug development," Nature Reviews Drug Discovery, 11(10):751-761 (2012).
Pustylnikov, et al., "Targeting the C-type lectins-mediated hostpathogen interactions with dextran," J Pharm Pharm Sci., 17(3):371-392 (2014).
Xu, et al., "Green fabrication of amphiphilic quaternized beta-chitin derivatives with excellent biocompatibility and antibacterial activities for wound healing," Advanced Materials, 30(29):1801100 (2018).

* cited by examiner

*Primary Examiner* — Po-Chih Chen
(74) *Attorney, Agent, or Firm* — Foley & Lardner LLP

(57) ABSTRACT

Provided herein are biodegradable polymers and nanoparticles comprising such polymers. The present nanoparticles deliver antibiotics to infected tissue with enhanced antibacterial efficacy. Thus, the present technology provides a nanoparticle comprising: a surface comprising one or more polysaccharides having specific binding affinity for bacteria; a core comprising a biodegradable polymer; and an antibacterial drug loaded within the core; wherein the biodegradable polymer comprises nitrogen-containing ionizable functional groups; the one or more polysaccharides having specific binding affinity for bacteria; and disulfide groups; the one or more polysaccharides are attached to the biodegradable polymer through phenyl boronic ester linkages; and the nanoparticle surface displays the polysaccharides such that the polysaccharide are available to bind to a bacterial cell surface.

11 Claims, 18 Drawing Sheets

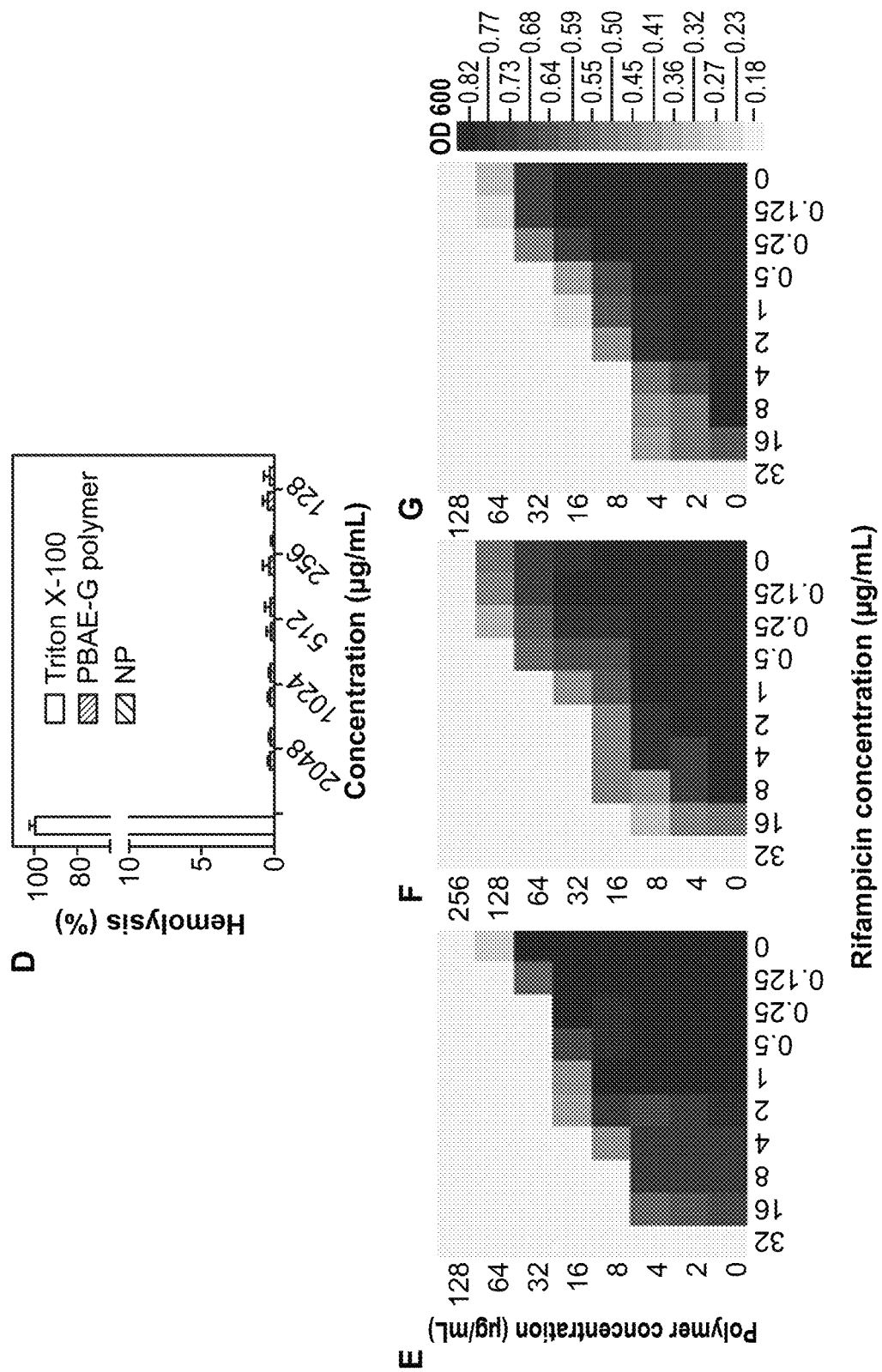
FIG. 2 (Cont. 1)

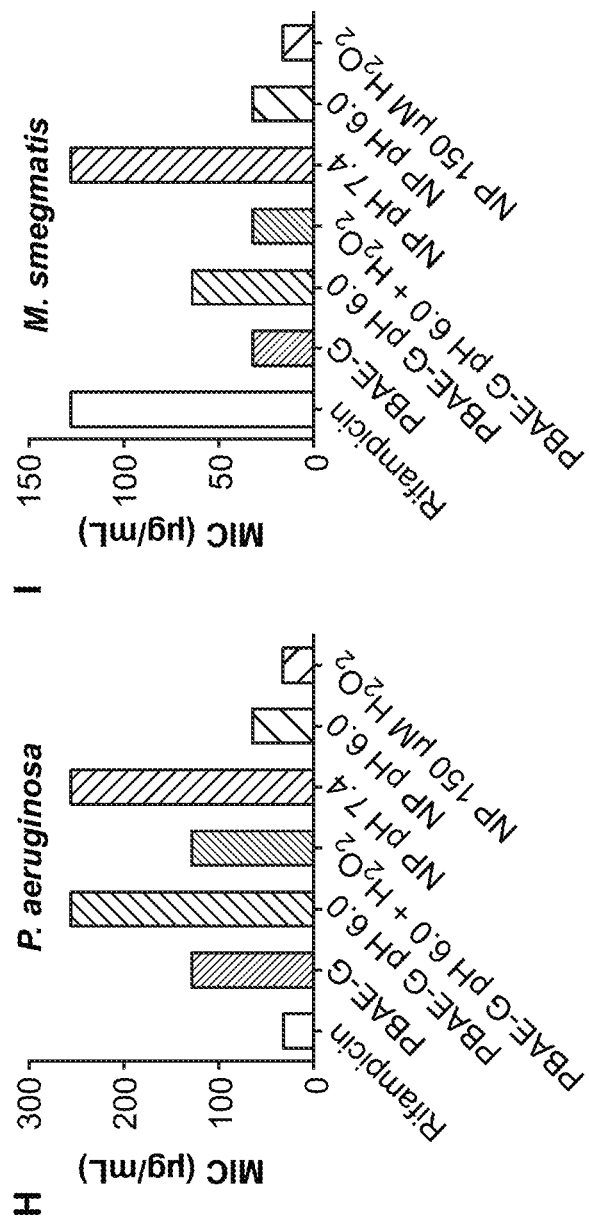
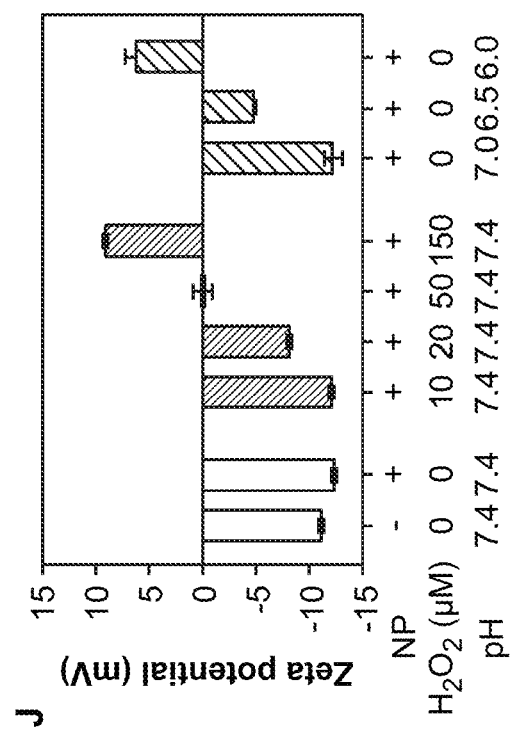
FIG. 2 (Cont. 2)

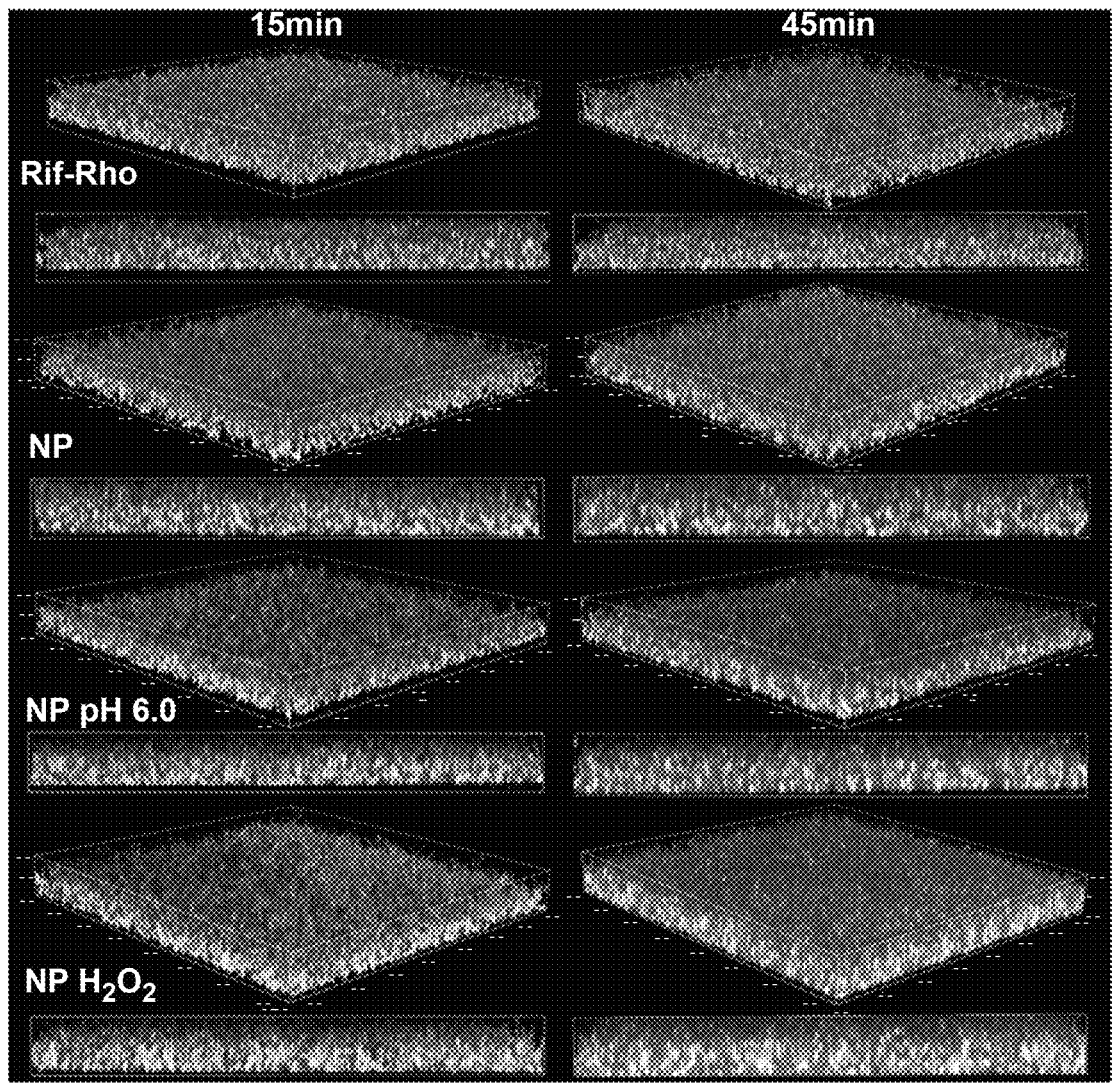
FIG. 4 (Cont. 1)

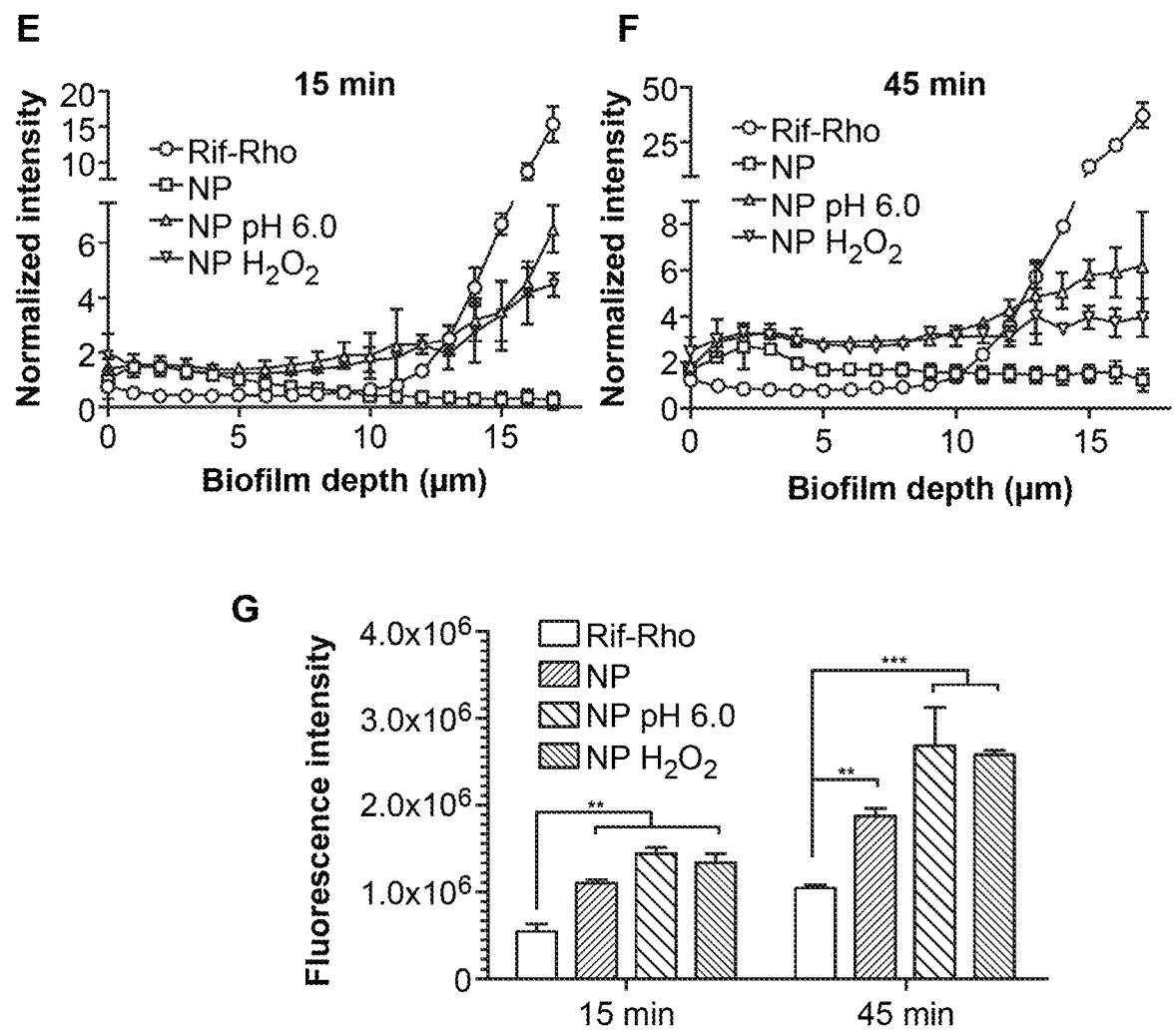
FIG. 4 (Cont. 2)

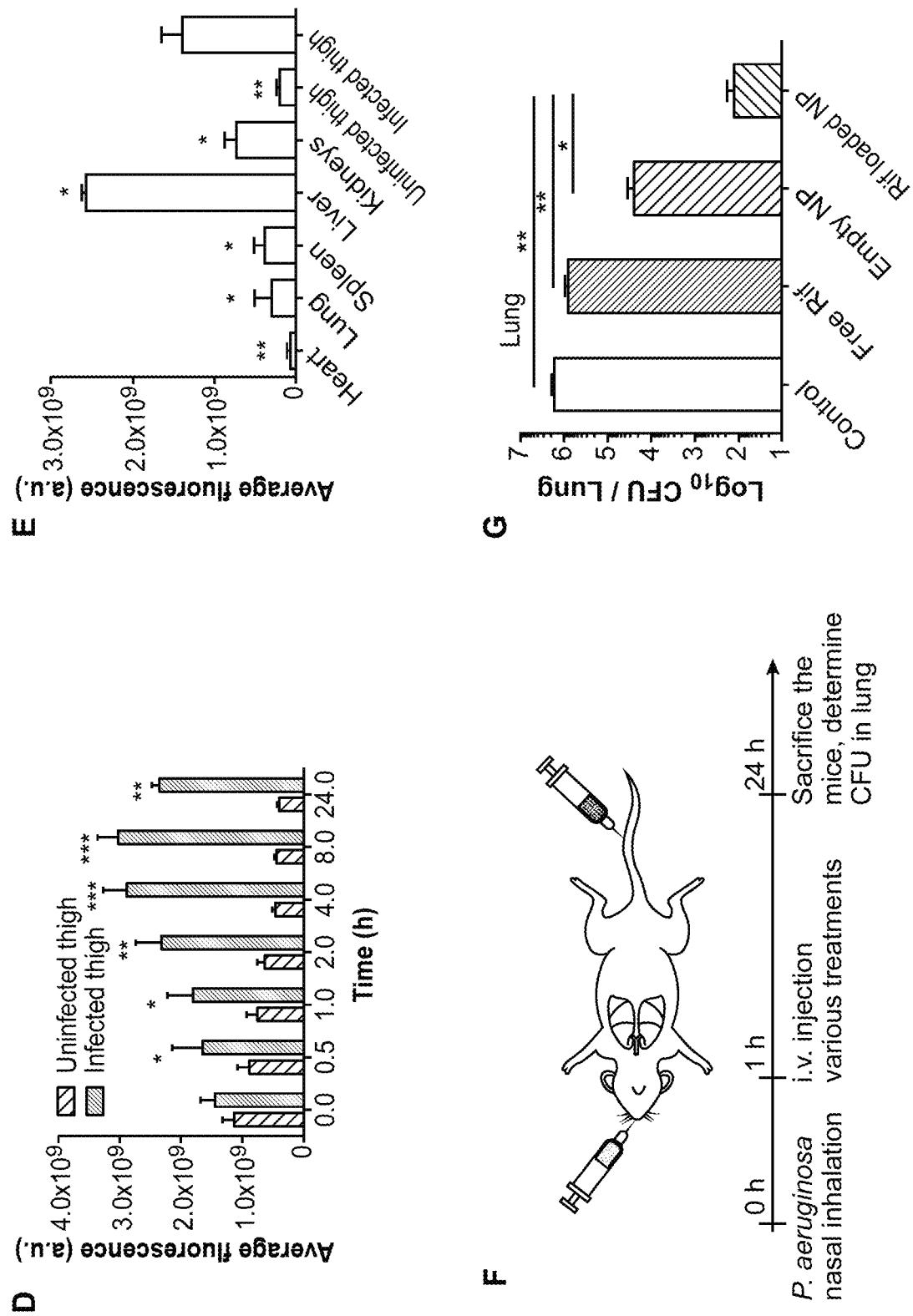
FIG. 6 (Cont. 1)

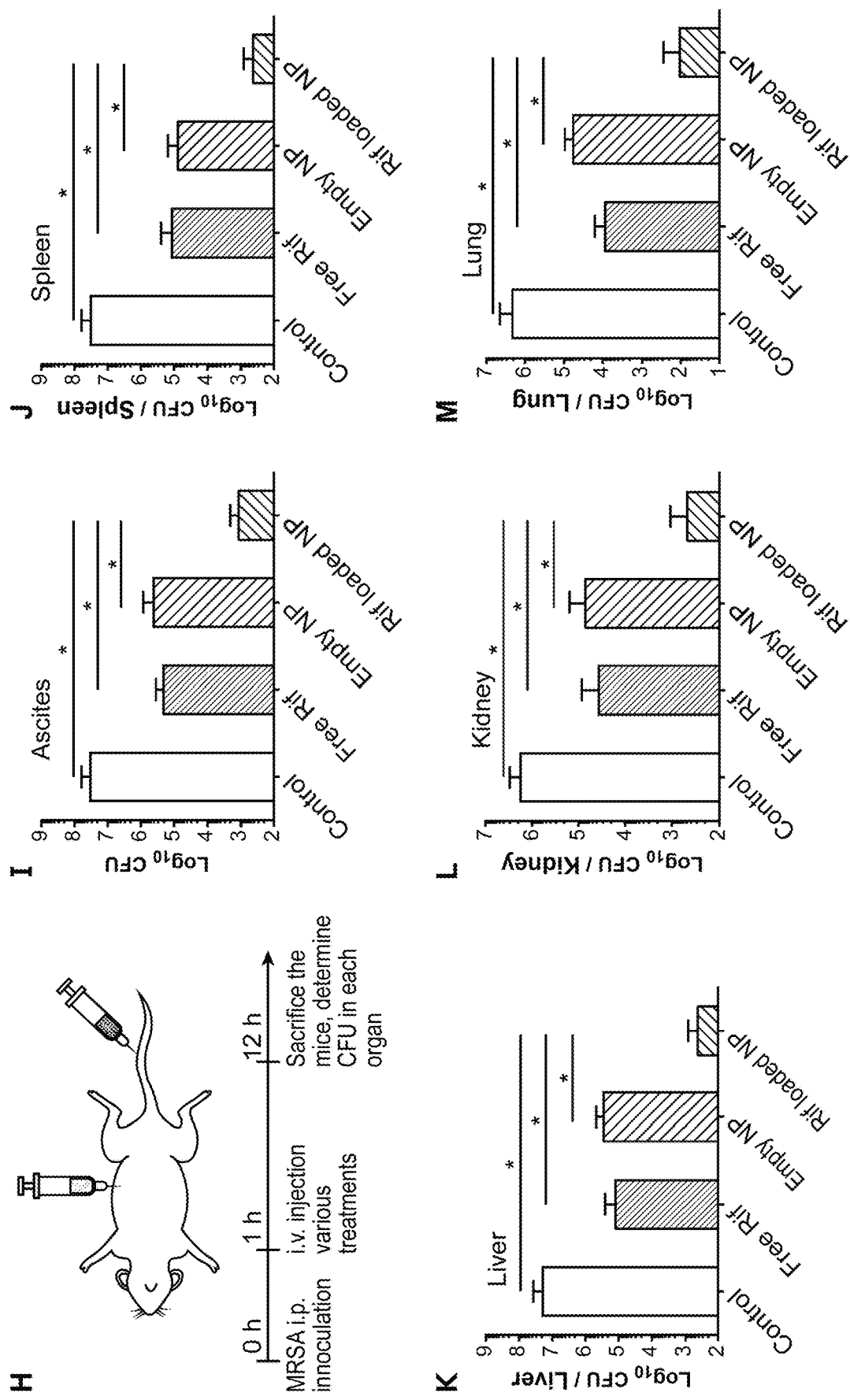
FIG. 6 (Cont. 2)

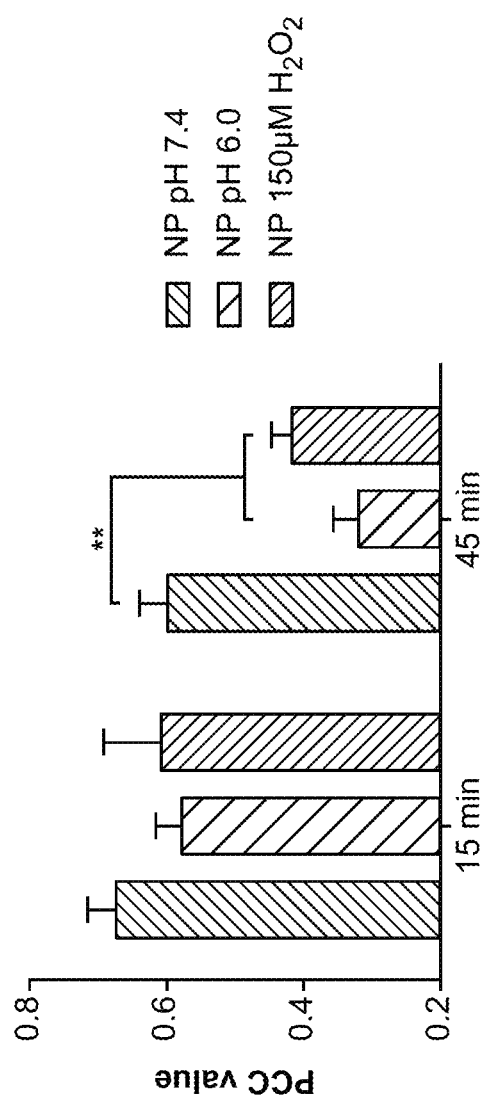
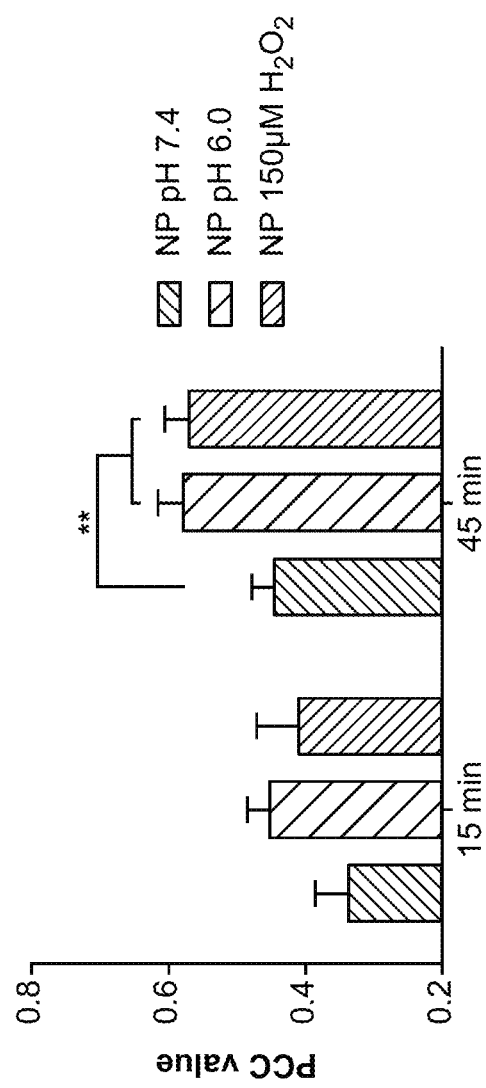
FIG. 9A
FIG. 9B

US 12,377,052 B2

DUAL-RESPONSIVE NANOPARTICLES FOR ENHANCED ANTIBACTERIAL EFFICACY

CROSS REFERENCE TO RELATED APPLICATION

This application claims the benefit of and priority to U.S. Provisional Application No. 63/094,783, filed on Oct. 21, 2020, the entire contents of which are incorporated herein by reference.

FIELD

The present technology relates generally to the field of nanoparticles for antibacterial drug delivery and enhanced efficacy. The present compositions provide a biodegradable polymer, a nanoparticle made from the polymer that can deliver antibacterials in response to the pH change and/or presence of reactive oxygen species (ROS) in the infected tissues. The nanoparticle has low toxicity for mammalian cells, but enhanced efficacy against biofilms and drug-resistant organisms.

BACKGROUND

Infectious diseases are a growing threat to public health due to increasing antimicrobial resistance (AMR) and stagnation in new antibiotic development. It is estimated that by the year 2050, AMR infection will be the leading cause of death worldwide and will kill over 10 million people each year if new solutions are not found. The complexity of infection, especially in chronic infectious diseases, necessitates the use of broad-spectrum antibiotics, which drives the selection of drug-resistant pathogens. Furthermore, it is increasingly challenging and costly to develop new antibiotics. In fact, no new class of antibiotics has been approved for treating Gram-negative bacteria caused infections since the 1980s.

AMR can be caused by decreased antibiotic uptake due to reduced permeability, and upregulated efflux pumps that expel the ingested chemicals. Such intrinsic AMR resistance allows the microbes to comprehensively resist various kinds of antibiotic treatments. Biofilms provide further protection to the microorganisms and significantly reduce their susceptibility to antibiotics by building up a resistant microenvironment and rejecting the penetration of the antibacterial agents. Additionally, pathogens can also acquire AMR through enzymatic degradation of antibiotics or alteration of the target proteins.

SUMMARY OF THE INVENTION

The present technology provides biodegradable polymers and nanoparticles (NP) comprising such polymers. The NP may be loaded with antibiotic drugs and used to treat drug-resistant bacterial infections. Thus, in any embodiments, the present technology provides nanoparticles comprising: a surface comprising one or more polysaccharides having specific binding affinity for bacteria; a core comprising a biodegradable polymer; wherein the biodegradable polymer comprises nitrogen-containing ionizable functional groups; the one or more polysaccharides having specific binding affinity for bacteria; and disulfide groups; the one or more polysaccharides are attached to the biodegradable polymer through phenyl boronic ester linkages; and the nanoparticle surface displays the polysaccharides such that the polysaccharide are available to bind to a bacterial cell surface. In any embodiments, the NP may include an antibacterial drug loaded within the core of the NP. Methods of making the biodegradable polymers and NP are also provided.

In another aspect, the present technology provides pharmaceutical compositions including the nanoparticles described herein with a pharmaceutically acceptable carrier or excipient.

In still another aspect, the present technology provides methods of using the NP disclosed herein. Thus, there are provided methods of treatment comprising administering to a subject suffering from a bacterial infection an effective amount of a drug-loaded nanoparticle as described herein in any embodiment. The present methods are especially useful for treating bacterial infections comprising a drug-resistant bacterial strain and/or a bacterial biofilm.

was loaded in the NP. MRSA (upper row) and *P. aeruginosa* (lower row) were stained with acridine orange (AO, green) and treated with free dextran-Cy5.5, free Rif-Rho, inactivated NP or NP activated under different pH or redox conditions (pH 6.0 or 150 µM hydrogen peroxide). White color resulted from the overlap of red, blue and green fluorescence signals. Scale bar: 10 µm (B) Colocalization of the bacteria (green) and Cy5.5 labeled PBAE-G polymer (blue). (C, D) Quantification of mean Rif-Rho fluorescence signal per bacterium for different treatments. (E) Colocalization analyses on the fluorescence between the bacteria and free dextran-Cy5.5, NP or free Rif-Rho, evaluated by Pearson's correlation coefficient (PCC). The PCC of the dextran group was calculated between the blue and green signals, while the PCC of the other two groups was determined between the red and green signals. (F) SEM images of the bacteria treated with PBS and NP under different pH and redox conditions (pH 6.0 or 150 µM hydrogen peroxide). The green arrows denote the intact NP attaching on the bacterial surface; the red arrows denote the defect on the bacteria cell wall and membrane induced by the cationic polymer. Scale bars: 1 µm. (G) AO/PI staining of MRSA (upper row) or *P. aeruginosa* (lower row) treated with PBS, free rifampicin or NP under different pH and redox conditions (pH 6.0 or 150 µM hydrogen peroxide). The green fluorescence (stained by AO) indicates that the cell membrane remains intact and the red fluorescence (stained by PI) indicates the disruption of the membrane. Scale bars: 10 µm.

Figure 4:
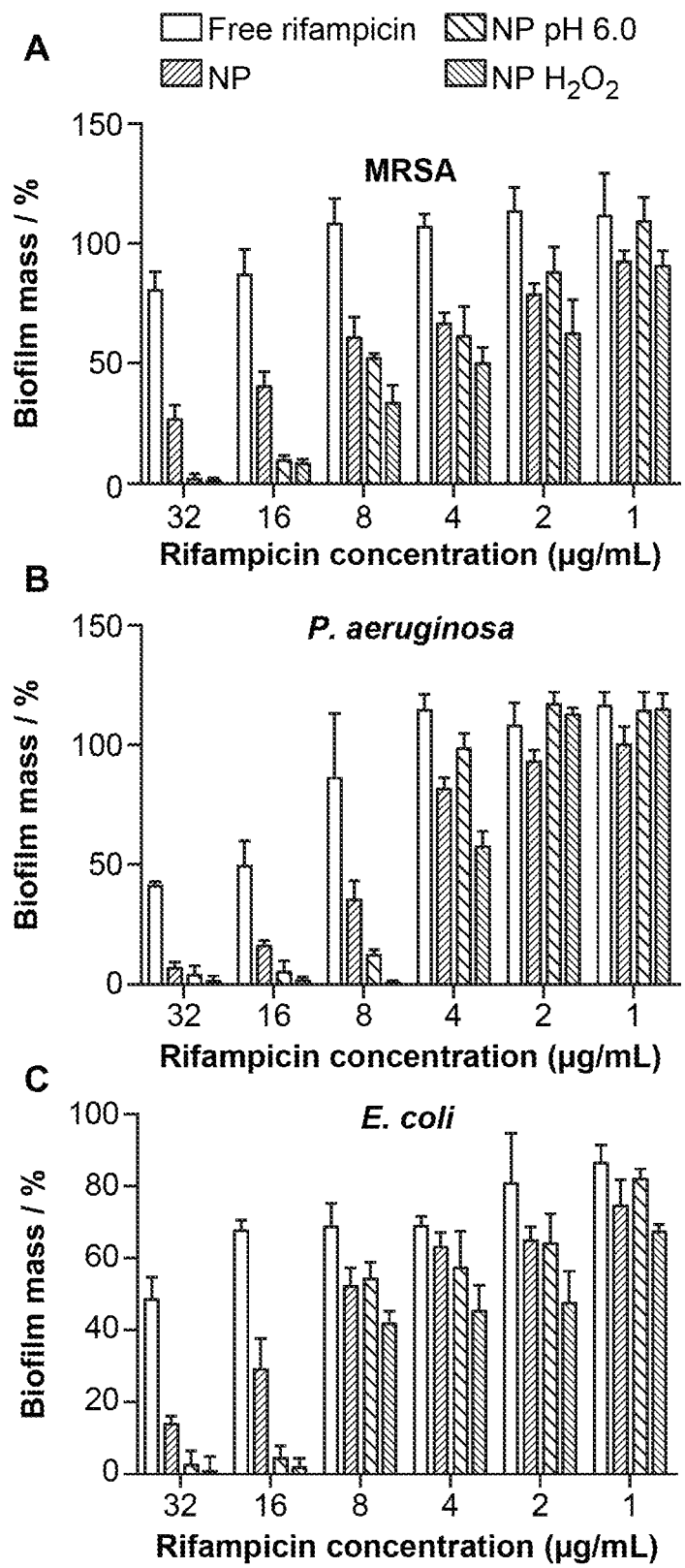

FIG. 4 shows data from an illustrative embodiment of the present technology: (A-C) Quantification of biofilms of MRSA (A), *P. aeruginosa* (B), and *E. coli* (C) treated with free rifampicin or NP. The biofilms were incubated with the NP under physiological (pH 7.4), acidic (pH 6.0) or oxidizing (150 µM hydrogen peroxide) conditions. (D) CLSM images of the MRSA biofilms incubated with rhodamine labeled rifampicin (Rif-Rho, red), or Rif-Rho loaded NP (constructed with dextran-Cy5.5, blue) under physiological (pH 7.4), acidic (pH 6.0) or oxidizing (150 µM hydrogen peroxide) conditions, for 15 min or 45 min. Bacteria in the biofilm were stained with AO (green). Dextran-Cy5.5 and Rif-Rho were employed to visualize the biofilm penetration capability of the NP and rifampicin, respectively, and their overlap reflected the drug release profile. (E, F) The penetration profiles of Rif-Rho in each group at 15 min (E) and 45 min (F). The value 0 µm on the x-axis indicates the bottom of the biofilm. (G) The total Rif-Rho fluorescence intensity in the biofilm for different treatments.

Figure 5:
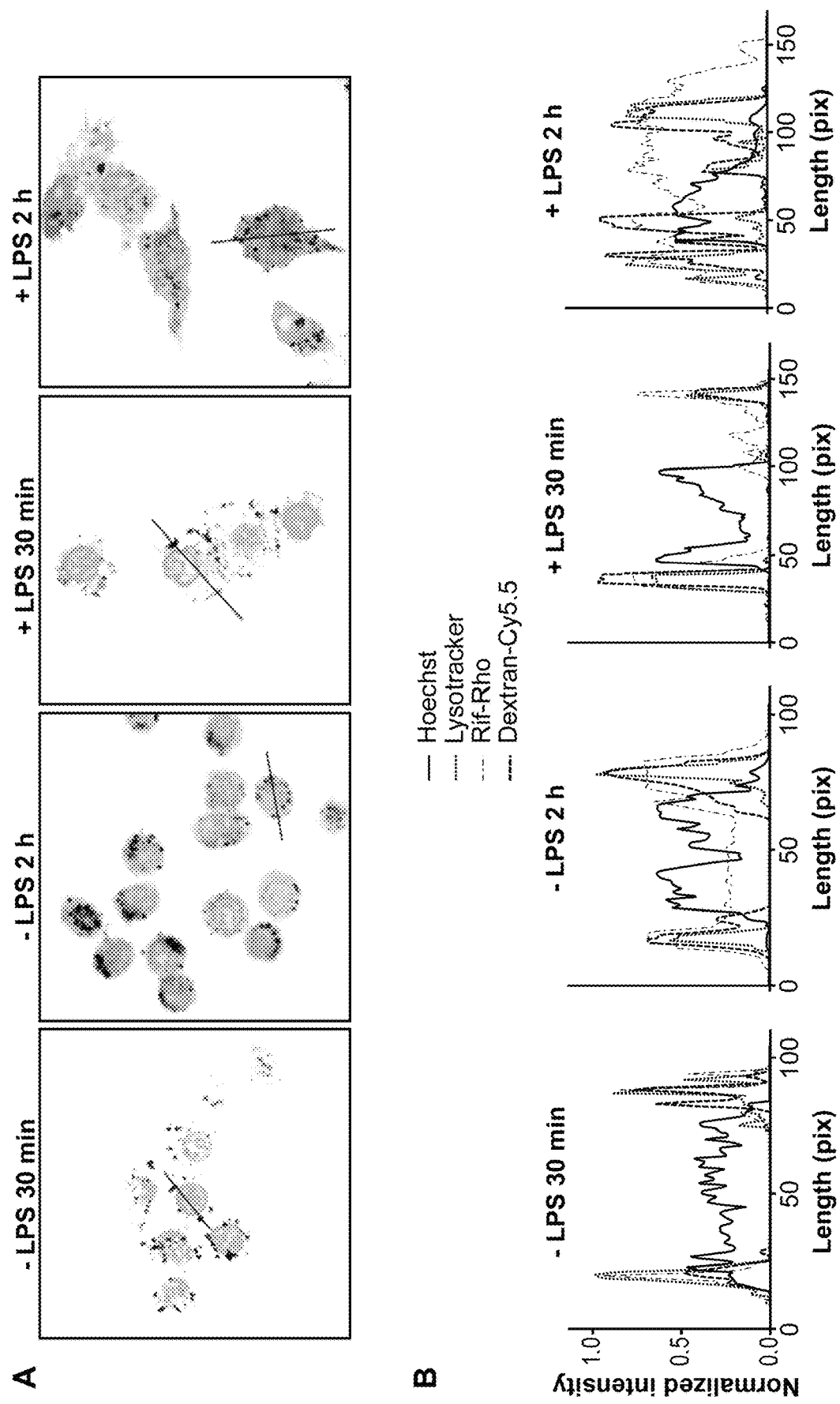
Figure 5:
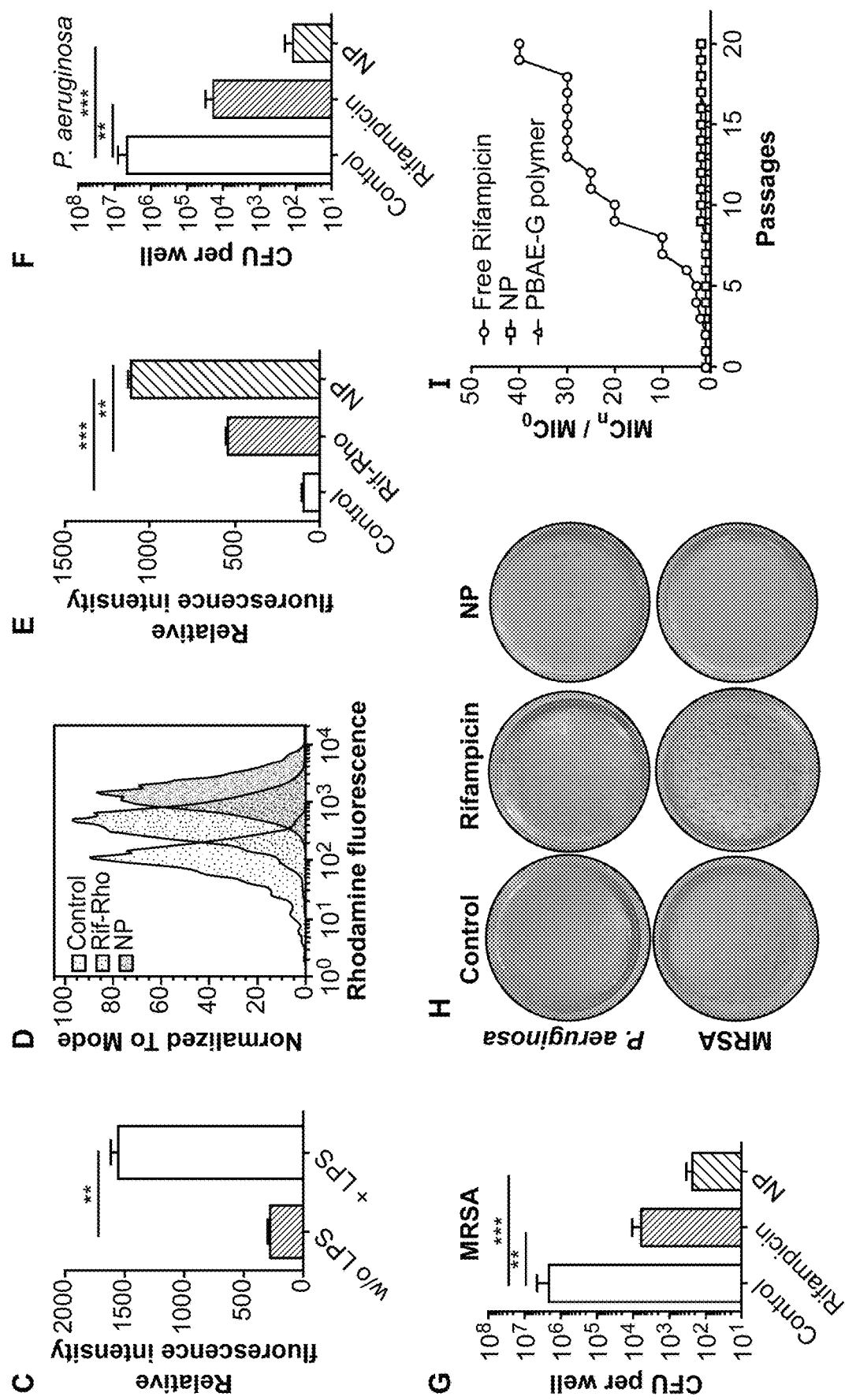

FIG. 5 (A) Subcellular localization of the Rif-Rho-loaded NP in RAW 264.7 cells. The cells with or without LPS (1 µg/mL) stimulation were incubated with the NP for 30 min and 2 h. Nucleus (blue) was stained with Hoechst 33342, while lysosome (green) was stained with Lysotracker green. Dextran-Cy5.5 (purple) and Rif-Rho (red) indicate the subcellular localization of the NP and the payload drug, respectively. Scale bars: 25 µm. (B) The fluorescence intensity profiles across the white lines in (A) for the four channels. (C) ROS levels in RAW 264.7 cells with or without LPS treatment, determined by DCF-DA. (D, E) Cellular uptake profile of free Rif-Rho and Rif-Rho-loaded NP in RAW 264.7 cells, monitored by flow cytometry. (F-H) CFUs of intracellular bacteria after different treatments. RAW 264.7 cells were seeded in 96-well plate and infected by *P. aeruginosa* (F) or MRSA (G). After removing planktonic bacteria, the cells were treated with free rifampicin or NP for one day, and then lysed by Milli-Q water containing 0.1% Triton X-100 (lyses the macrophages without damaging the bacteria). (H) CFU in each well was determined by serial dilution. (I) Drug resistance development profiles of *E. coli* (ATCC 25922) during serial passaging in the presence of sub-MIC dosage of free rifampicin, PBAE-G or NP. The y-axis indicates the folds of increased MIC compared to the initial ones.

Figure 6:
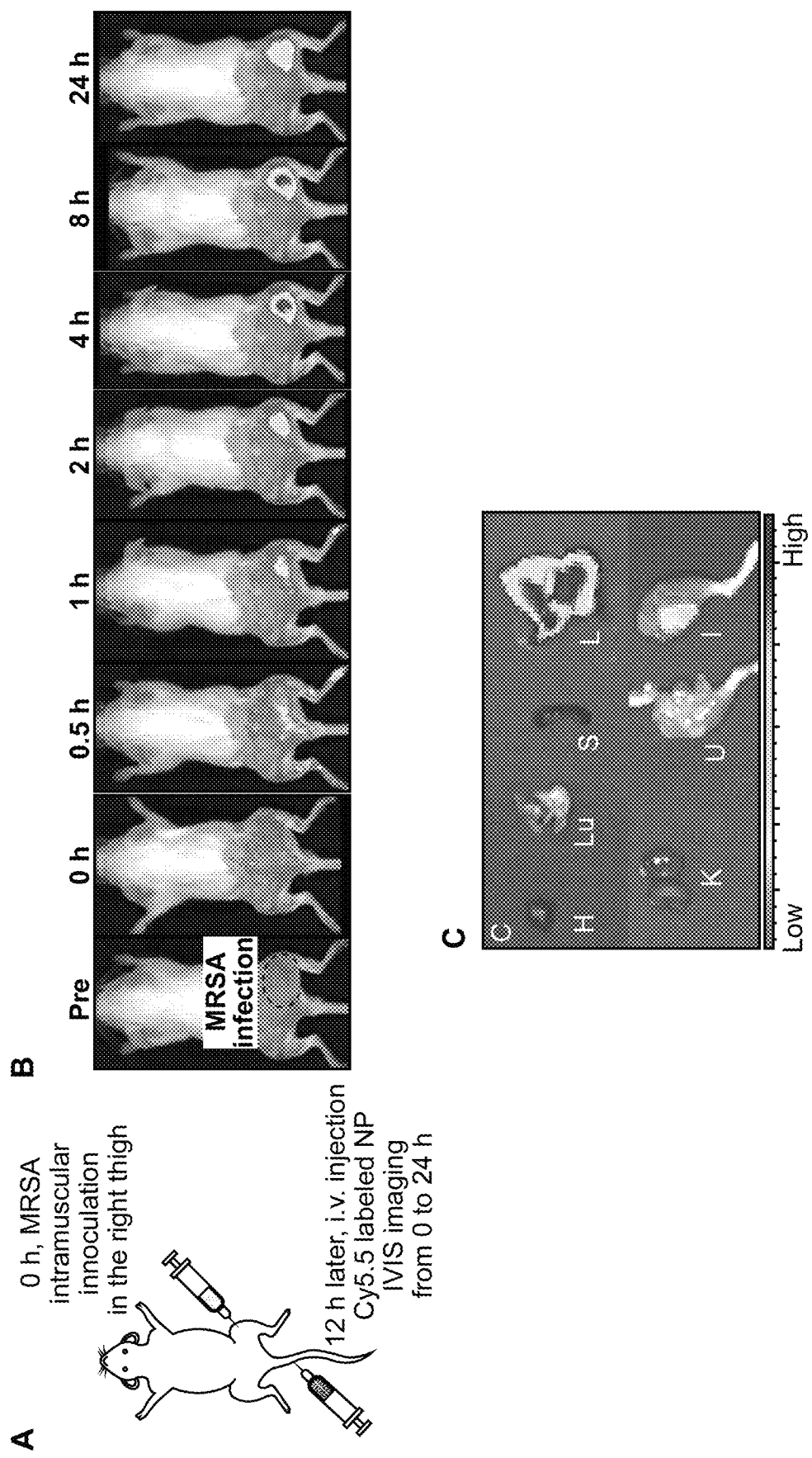

FIG. 6 (A) Schematic illustration of the experimental procedures for the MRSA thigh infection model. (B) Fluorescence images of mouse with MRSA infection on its right thigh. Cy5.5-labeled NP (PBAE-G-Cy5.5) was administrated through i.v. injection. The uninfected left thigh was used as a negative control. (C) Ex vivo fluorescence images for the major organs and tissues of the MRSA infected mouse were collected 24 h post-treatment. H, Lu, S, L, K, U and I represent heart, lung, spleen, liver, kidney, the uninfected thigh, and the MRSA-infected thigh, respectively. (D) Comparison of the fluorescence intensity in the MRSA-infected leg with the uninfected leg at scheduled time points. (E) Quantitative analysis of the mean fluorescence intensity per organ or tissue in the ex vivo image. Statistical analysis was done for each organ relative to the infected thigh group (n=3). (F) Experimental procedures for the antimicrobial efficacy study in the *P. aeruginosa* lung infection model. (G) Bacteria burden of mice with *P. aeruginosa* lung infection. A single injection of different treatments (PBS, free rifampicin, empty NP, or rifampicin-loaded NP) was given intravenously 1 h after the infection. The infected lungs were collected 24 h after the injection. After homogenization, the amount of CFU was determined through serial dilution. (H) Experimental procedures for the antimicrobial efficacy study in the MRSA peritonitis model. (I-M) Therapeutic efficacy of various treatments in the mouse peritonitis model. CFU in ascites, spleen, liver, kidneys and lung were determined 12 h after the infection. * $p<0.05$,  $p<0.01$ and * $p<0.001$, respectively.

Figure 7:
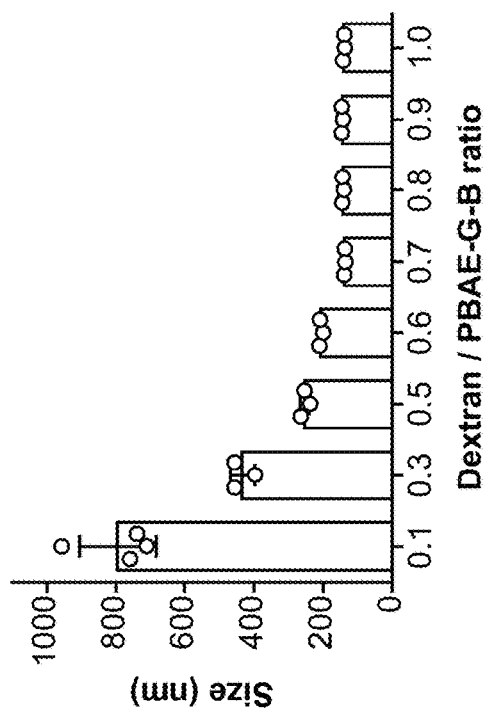

FIG. 7 shows the effect of the dextran to PBAE-G-B polymer ratios on the resulting nanoparticle sizes measured by DLS.

Figure 8:
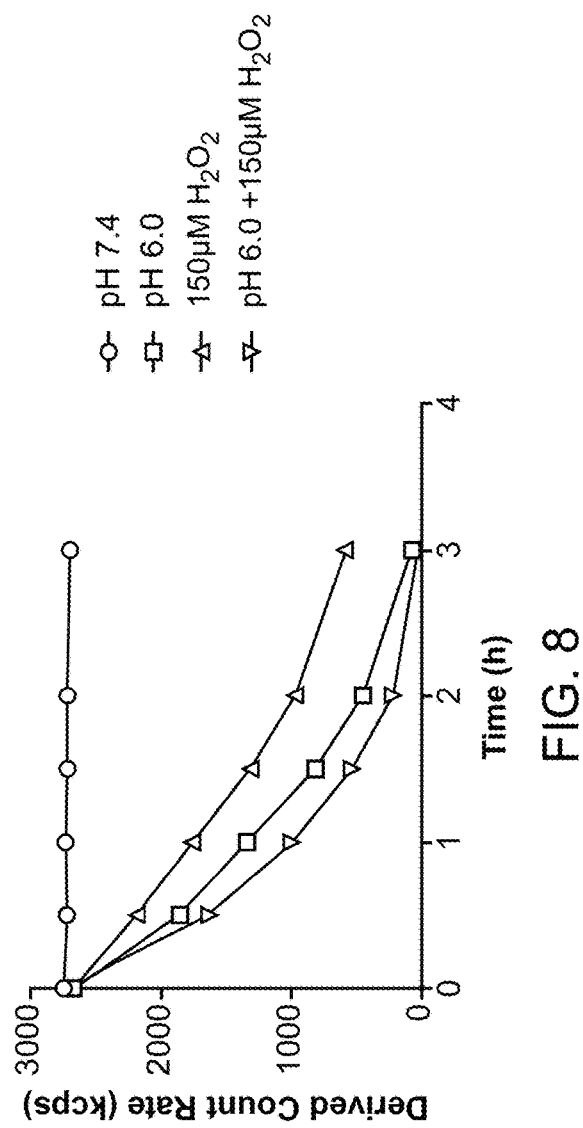

FIG. 8 Count rates of the NPs incubated under physiological (pH 7.4), acidic (pH 6.0) and/or oxidizing (150 µM hydrogen peroxide) conditions, measured by DLS.

Figure 9C:
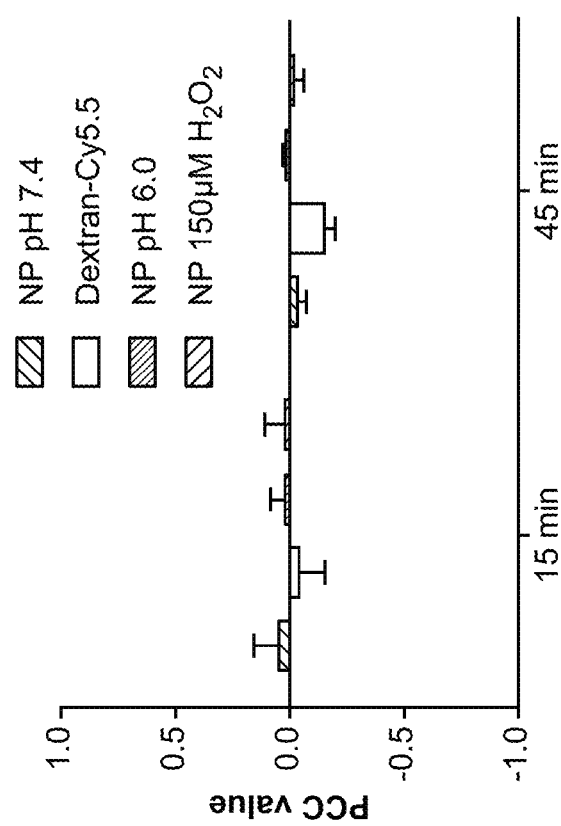

FIGS. 9A-C 9A Colocalization analysis between the Cy5.5-labeled NP blue signal and the Rif-Rho red signal when the biofilm was treated with the NP under physiological (pH 7.4), acidic (pH 6.0), or oxidizing (150 µM hydrogen peroxide) conditions. The reduced PCC between the NP and Rif-Rho indicated drug release. 9B: Colocalization analysis between the bacteria green signal and Rif-Rho red signal when the biofilm was treated with the NP under physiological (pH 7.4), acidic (pH 6.0) or oxidizing (150 µM hydrogen peroxide) conditions. 9C: Colocalization analysis between the bacteria green signal and dextran blue signal when the biofilm was treated with free dextran-Cy5.5 or NP under physiological (pH 7.4), acidic (pH 6.0) and oxidizing (150 µM hydrogen peroxide) conditions.

DETAILED DESCRIPTION

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 5 kD" would mean "5 kD±0.5 kD" or "4.5 kD to 5.5 kD."

"Effective amount" refers to the amount of composition (e.g., the biodegradable polymer, antibiotic or NP) required to produce a desired effect. Hence, an effective amount of a compound or composition of the present technology in the context of treatment (i.e., "a therapeutically effective amount") refers to an amount of the compound or composition that alleviates, in whole or in part, symptoms associated with a disorder or disease, or slows or halts further progression or worsening of those symptoms. In the context of prevention, an effective amount prevents or provides prophylaxis for the disease or disorder in a subject at risk for developing the disease or disorder. One example of an effective amount includes amounts or dosages that yield acceptable toxicity and bioavailability levels for therapeutic (pharmaceutical) use including, but not limited to, the treatment of a bacterial infection, including infections by Gram-positive or Gram-negative bacteria. Determining a therapeutically effective amount of a compound described herein for treating a particular disorder or disease is well within the skill in the art in view of the present disclosure.

"Molecular weight" as used herein with respect to polymers refers to weight average molecular weights (Mw) and can be determined by techniques well known in the art including gel permeation chromatography (GPC). GPC analysis can be performed, for example, on a D6000M column calibrated with poly(methyl methacrylate) (PMMA) using triple detectors including a refractive index (RI) detector, a viscometer detector, and a light scattering detector, and dimethylformamide as the eluent.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydrobromic acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

As used herein, a "subject" or "patient" is any animal subject to bacterial infections. In any embodiments, the subject is a mammal, such as a cat, dog, ungulate, rodent or primate. In any embodiments, the subject is a human. The term "subject" and "patient" can be used interchangeably.

"Treating" or "treatment" within the context of the present technology, means an alleviation, in whole or in part, of symptoms associated with a disorder or disease, or slowing, or halting of further progression or worsening of those symptoms. As a non-limiting example of treatment, a subject can be successfully treated for a bacterial infection if, after receiving through administration an effective or therapeutically effective amount of one or more NPs or compositions described herein, the subject shows observable and/or measurable reduction in or absence of one or more signs and symptoms of the infection such as, but not limited to, reduction or elimination of bacterial load, fever, headache, nausea, vomiting, runny nose, and cough, increased energy, or improvement in quality of life relating thereto. Treatment, as defined herein, of a subject, including a human being, is subject to medical aid with the object of improving the subject's condition, directly or indirectly. Treatment typically refers to the administration of an effective amount of an NP or pharmaceutical composition including the NP as described herein.

In one aspect, the present technology provides a nanoparticle comprising a surface including one or more polysaccharides having specific binding affinity for bacteria and a core comprising a biodegradable polymer. The present technology also provides nanoparticles having an antibacterial drug loaded within the core. The biodegradable polymer (also referred to as the "cationic polymer" herein) includes nitrogen-containing ionizable functional groups; one or more polysaccharides having specific binding affinity for bacteria; and disulfide groups. The nanoparticle surface includes (e.g., displays) the one or more polysaccharides such that the one or more polysaccharides are available to bind to a bacterial cell surface. In some embodiments, the one or more polysaccharides are attached to the biodegradable polymer through phenyl boronic ester linkages. The nanoparticle may be configured to be stable in aqueous solution at pH 7.4 but may be unstable at a pH below 7 or in the presence of reactive oxygen species. In another aspect, the present technology provides biodegradable polymers that may be used to form the instant nanoparticles.

In any embodiments of the biodegradable polymer or nanoparticle, the nitrogen-containing ionizable functional groups are present in a backbone of the polymer, in one or more side-chains of the polymer, or in both the backbone and one or more side-chains of the polymer. The nitrogen-containing ionizable functional groups may include one or more amine, amidine, guanidine, ammonium, amidinium, and/or guanidinium groups. In any embodiments, the nitrogen-containing ionizable functional groups may include one or more of amine, ammonium, guanidine and/or guanidinium groups.

In any embodiments of the biodegradable polymer or nanoparticle, the biodegradable polymer may be a polyester, polyamide, polypeptide, polyurethane, polyurea, or a combination of any two or more thereof. In any embodiments the polymer may be a polyester, for example, a poly(beta amino ester). The biodegradable polymer may be a poly(beta amino ester) comprising guanidine-containing sidechains, phenylboronic acid-containing side chains, and/or phenyboronic ester-containing side chains. The polymer may also be branched or unbranched (i.e., linear); in any embodiments it may be a copolymer such as a block copolymer, a graft copolymer, or a random copolymer. In any embodiments the polymer may be linear, such as a linear polyurea or a linear polyurethane. In any embodiments, the polymer may include one or more disulfide bonds in a backbone of the polymer. In any embodiments, the polymer may have a weight average molecular weight of about 1 kD to about 40 kD, including, without limitation, about 1 kD, about 2 kD, about 3 kD, about 4 kD, about 5 kD, about 6 kD, about 7 kD, about 8 kD, about 9 kD, about 10 kD, about 15 kD, about 20 kD, about 25 kD, about 30 kD, about 35 kD, about 40 kD, or a range between and including any two of the foregoing values. For example, the polymer may have a weight average molecular weight of about 1 kD to about 20 kD, about 2 kD to about 20 kD, or about 5 kD to about 15 kD. In any embodiments, the polymer may have a weight average molecular weight of about 10 kD.

In any embodiments of the biodegradable polymer or nanoparticle, the biodegradable polymer may include a repeating subunit of Formula I:

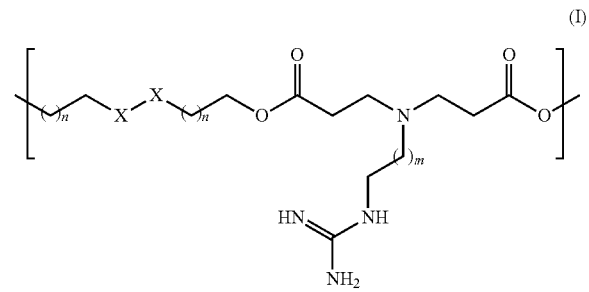

(I)

wherein
X—X is S—S or $CH_2$—$CH_2$;
each n is independently 0, 1, 2, 3, 4, 5, or 6, provided that when X—X is S—S, n is not 0; and
each m is 1, 2, or 3.

It will be understood that the repeating subunits need not be consecutively attached to each other. In any embodiments of the biodegradable polymer including repeating subunits of Formula I, X—X may be S—S, and each n is independently 1, 2, 3, 4, 5, or 6. In any embodiments, X—X may be $CH_2$—$CH_2$. In any such embodiments, each n may independently be 0, 1, 2 3 or 4. In any such embodiments, each n may be 0. In any embodiments, each n may be 1. In any embodiments, each m may be 1. In any embodiments, each m may be 2, and in any embodiments, each m may be 3.

In any embodiments of the biodegradable polymer or nanoparticle, the biodegradable polymer may include a repeating subunit of Formula II:

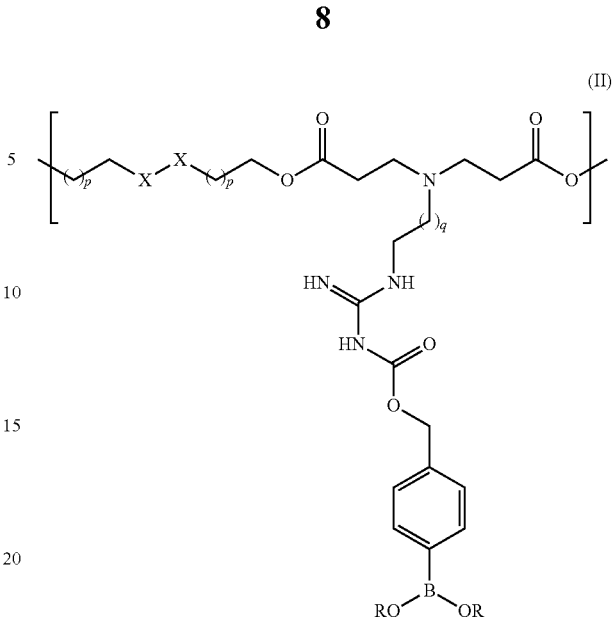

(II)

wherein
X—X is S—S or $CH_2$—$CH_2$;
each R is independently H or a polysaccharide selected from the group consisting of dextran, mannan, fucoidan, heparin and a combination of any two or more thereof;
each p is independently 0, 1, 2, 3, 4, 5, or 6, provided that when X—X is S—S, p is not 0; and
each q is 1, 2, or 3.

In any embodiments of the biodegradable polymer including repeating subunits of Formula II, each R may be independently H or dextran. In any embodiments each R is H. In any embodiments, X—X may be $CH_2$—$CH_2$. In any such embodiments, each p may independently be 0, 1, 2 3 or 4. In any such embodiments, each p may be 0. In any embodiments, each p may be 1. In any embodiments, each q may be 1. In any embodiments, each q may be 2, and in any embodiments, each q may be 3. In any embodiments the biodegradable polymer may include repeating subunits of both Formula I and Formula II.

Polysaccharides of the present technology are selected for their specific binding affinity for bacteria (in contrast to non-specific binding affinity). By specific binding affinity is meant the binding affinity (kD) between the polysaccharide and its bacterial binding partner. While not wishing to be bound by theory, polysaccharides known to specifically bind to certain lectins may be used. Thus, in any embodiments of the biodegradable polymer or nanoparticle, the polysaccharides may be selected from the group consisting of dextran, mannan, fucoidan, heparin, and a combination of any two or more thereof. In any embodiments, the one or more polysaccharides may be dextran. In any embodiments, the one or more polysaccharides have a weight average molecular weight of 3 kD to 300 kD. For example the one or more polysaccharides may have a weight average molecular weight of 3 kD, 4 kD, 5 kD, 10 kD, 15 kD, 20 kD, 25 kD, 50 kD, 100 kD, 150 kD, 200 kD, 250 kD, 300 kD or a range between and including any two of the foregoing values, e.g., 3 kD to 150 kD or 5 kD to 50 kD. In any embodiments, the polysaccharides may have a kD for bacteria (including, e.g., bacterial lectins) of about 1 mM or less, less than 1 mM, less than 100 uM, less than 10 uM, or less than 5 uM, or less than 1 uM. In some embodiments, the polysaccharides may have a kD for bacteria (including, e.g., bacterial lectins) of less than 100 uM, e.g., from any of 0.1 nM, 1 nM, 10 nM or 100 nM, to less than 100 uM.

A variety of antibiotics may be used in the nanoparticle of the present technology so long as they have both sufficient water solubility and potency so that when released in infected tissue, the antibiotic reaches therapeutically effective concentrations. In any embodiments, the antibiotic may be one or more of rifampicin, gentamycin, streptomycin, clindamycin, tetracycline, erythromycin, ciprofloxacin, sulfathiazole, spectinomycin, roxithromycin, sisomicin, novobiocin, isoniazide, clarithromycin, salinomycin, or roxithromycin. In any embodiments, the antibiotic may be rifamipicin.

The biodegradable polymers described herein may be prepared by polymerization and coupling methods known in the art. In any embodiments a disulfide compound that contains at least two amine or hydroxyl groups (e.g., 2,2'-dithio-diethanol, 2,2'-dithio-ethanediamine, 3,3'-dithio-propanediol, etc.) may be reacted with an acrylate derivative to form a bis acrylate ester or bis acrylamide. Alternatively a diol or diamine (e.g., butane-1,4-diol, butane-1,4-diamine pentane-1,5-diol, etc.) may be reacted with an acrylate derivative to form a bis acrylate ester or bis acrylamide. In any embodiments, polymer may be formed from the diacrylate by Michael addition of a suitable amine, including an amine bearing a substituent such as a halogen or an optionally protected functional group. Non-limiting examples of suitable amines include N-Boc-ethylene/propylene/butylene/pentylene/hexylene diamine, N-Fmoc-ethylene/propylene/butylene/pentylene/hexylene diamine, allylamine, 2-hydroxyethylamine, etc. In any embodiments, the amine may be N-Boc-ethylene diamine, and reacts with two acrylate groups in the presence of non-nucleophilic base (e.g., a tertiary amine base) to provide a polymer bearing N-Boc aminoethyl sidechains. The Boc group may be deprotected in the normal ways with acid (e.g., HCl/dioxane or TFA) to provide the amine salt. Various groups may be coupled to the amine to provide additional ionizable nitrogen-containing groups. For example, amidine (via 1H-pyrazole-1-carboxamidine and DIPEA) may be coupled with the amine to give guanidine. Phenyl boronic acid groups may be coupled to the amine or, advantageously, to the guanidine group. For example phenylboronic acid chloroformate may be coupled to the amine or the guanidine. The phenylboronic acid is typically introduced in protected for, e.g., as a pinacol ester. The pinacol groups on the polymer may be readily protected by, e.g., diethanolamine. Using the foregoing procedures, a biodegradable polymer, optionally containing disulfide groups and having, e.g., repeating subunits of Formula I and/or II, may be prepared. It will be understood that the amounts of amines and diacrylates may be varied to produce polymers of various sizes. It will be appreciated that those of skill in the art will be able to select the types and amounts of amines in view of the present disclosure and general knowledge in order to prepare biodegradable polymers of the present technology.

The present NPs may be of various sizes, e.g., from 10 nm to less than 1 μm. In any embodiments, the NPs may have an average diameter of 10 nm, 25 nm, 50 nm, 75 nm, 100 nm, 125 nm, 150 nm, 200 nm, 300 nm, 400 nm, 500 nm, 600 nm, 700 mn, 800 nm, 900 nm, less than 1 μm, or a range between any two of the foregoing values. For example, the NPs my have an average diameter of 75 nm to 200 nm.

Figure 1:
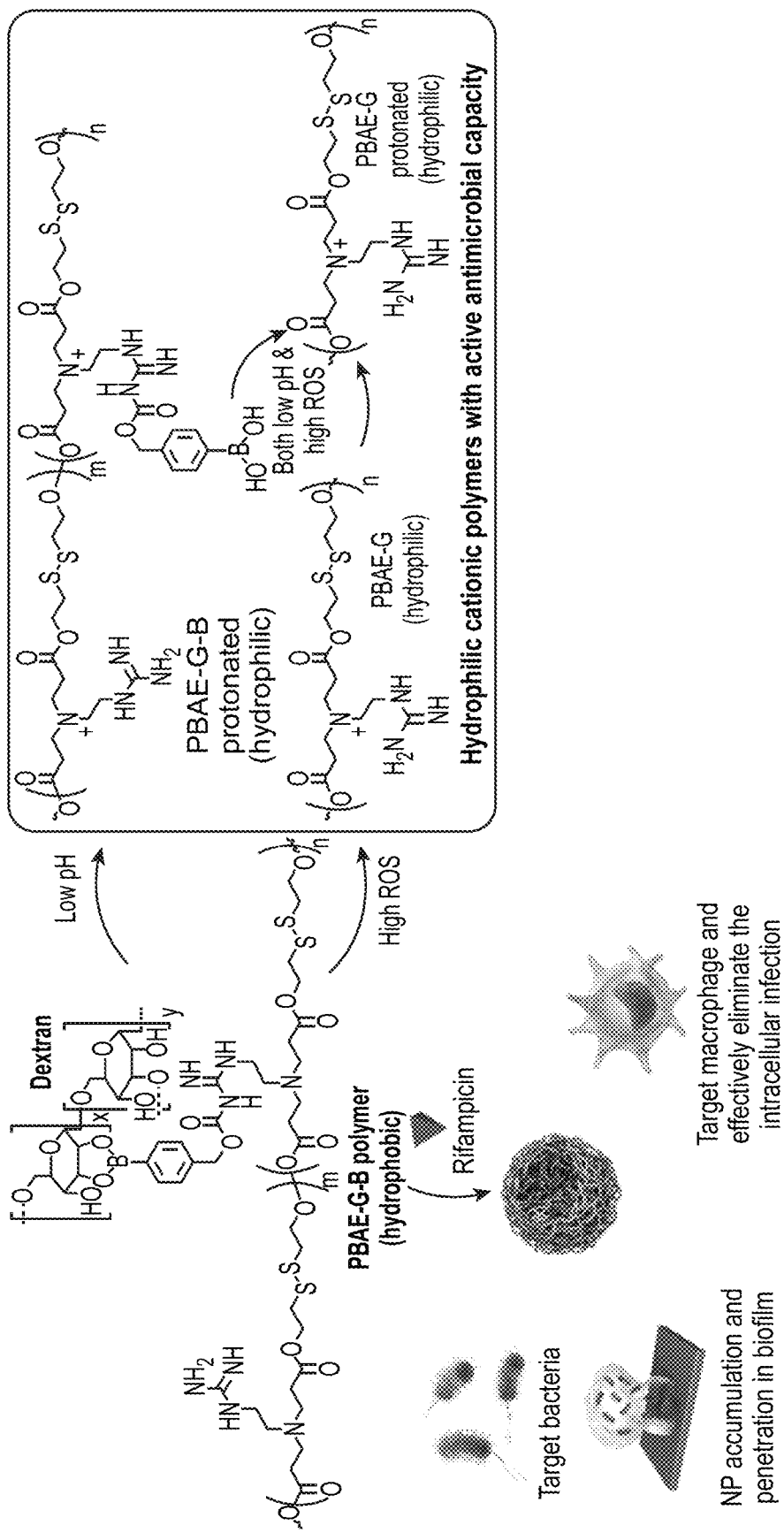
FIG. 1 shows a schematic illustration of a dual responsive nanoparticle (NP) of the present technology. The NP accumulates in the infected tissues through the enhanced permeability and retention (EPR) effect. The dextran coating of the NP enhances the retention of the NP in the infected tissues via the interaction between the dextran and the bacterial lectin. The NP is activated by low pH and/or high ROS, unique features of the infection microenvironment, and releases antibiotic and cationic antimicrobial polymers. The released cationic polymers can agglomerate the pathogens, while entrapping the antimicrobial materials in the microbe cluster. The cationic polymers also show a synergistic effect with the antibiotic and diminish the intrinsic resistance of the AMR pathogens by perturbing the bacterial membrane and thereby enhancing the transport of antibiotic into the bacteria. The NP enables the antibiotic to penetrate both bacterial biofilms and mammalian cells, thus allowing the elimination of biofilm and intracellular infections. After it functions, the polymer with disulfide groups in its backbone can be readily degraded in mammalian cells to reduce systemic toxicity.
Figure 1:
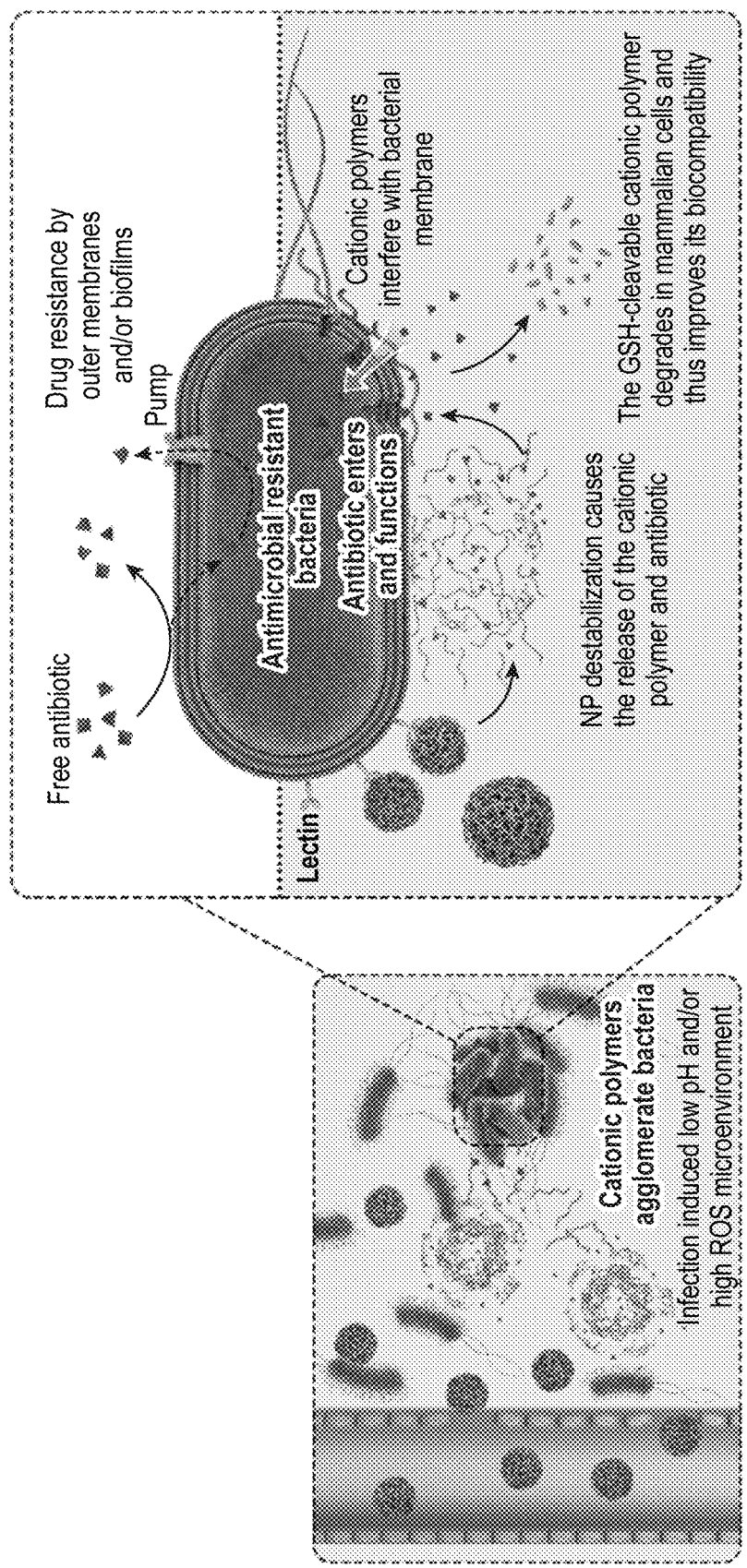

The present biodegradable polymer and nanoparticles formed therefrom permit the delivery of antibiotics to drug-resistant bacteria with increased efficacy. While not wishing to be bound by theory, the efficacy of the disclosed nanoparticles in treating bacterial infection (including drug-resistant infections) is believed to rest on several features. As shown in FIG. 1, an illustrative embodiment of the present technology, drug-resistant bacteria often block antibiotics from crossing the bacterial cell wall/membrane (including by forming biofilms) and/or pump them back outside into the extracellular environment if they do get in. The present dual responsive nanoparticles which include a biodegradable polymer (i.e., one that degrades in the presence of target bacteria) can counteract these bacterial strategies.

The present NPs show strong affinity with a variety of pathogens and effectively accumulate in tissues infected by bacteria. This is in part likely due to the EPR effect, and in part due to the specific binding affinity of the polysaccharides on the surface of the NPs for lectins on bacterial cell surfaces. The low pH and/or high concentration of reactive oxygen species (ROS) in the infectious microenvironment, activate the NPs to release both cationic polymer (due to the nitrogen-containing ionizable functional groups) and antibiotic. The low pH of infected tissue (near, e.g., pH 6) protonates the ionizable nitrogen-containing functional groups such as, in one embodiment, the tertiary amine in the polymer backbone, destabilizing the NP. At the same time, the phenyl boronic ester linkage to the one or more polysaccharides is cleaved by hydrolysis at low pH and alternatively, by oxidation via ROS, also destabilizing the NP. As the NP degrades, both the antibiotic and the positively charged polymer are released. The polymer's strong positive charge facilitates interactions of the NP with the negatively charged bacterial surface, inducing pores on the bacterial wall/membrane and damaging the bacteria. The antibiotic cannot be excluded and is able to cross the bacterial cell membrane. If it is pumped out, the antibiotic is able to diffuse back into the bacterial cell due to the disrupted membrane. Together, the biodegradable polymer and antibiotic display additive and often synergistic activity against AMR pathogens.

The NP formulation demonstrates both safety and efficacy in two animal infection models against either gram-negative or gram-positive AMR pathogens. The combined effect of the cationic polymer and antibiotic of the NP acts to diminish the drug resistance of pathogens, leading to significantly enhanced antibacterial efficacy while minimizing the required NP dosage. The NP is also more biocompatible than normal cationic polymers. When the polymer encounters a reducing environment, such as the interior of a mammalian cell with glutathione, the disulfide bonds of the polymer are cleaved, degrading the polymer into smaller subunits, which have less toxicity.

The present technology provides pharmaceutical compositions and medicaments comprising any one of the embodiments of the nanoparticles disclosed herein and one or more pharmaceutically acceptable carriers or excipients. The compositions may be used in the methods and treatments described herein. The pharmaceutical composition may include an effective amount of any of one of the embodiments of the compositions disclosed herein for treating a bacterial infection in a subject.

The compositions described herein can be formulated for various routes of administration, for example, by parenteral, rectal, nasal, vaginal administration, or via implanted reservoir. Parenteral or systemic administration includes, but is not limited to, subcutaneous, intravenous, intraperitoneal, and intramuscular injections. The following dosage forms are given by way of example and should not be construed as limiting the instant present technology.

Injectable dosage forms generally include solutions or aqueous suspensions which may be prepared using a suitable dispersant or wetting agent and a suspending agent so long as such agents do not interfere with formation of the NPs described herein. Injectable forms may be prepared with acceptable solvents or vehicles including, but not limited to sterilized water, Ringer's solution, 5% dextrose, or an isotonic aqueous saline solution.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. Thus, the present technology provides a pharmaceutical composition comprising any NP as described herein and a pharmaceutically acceptable carrier or excipient.

Specific dosages may be adjusted depending on conditions of disease, the age, body weight, general health conditions, sex, and diet of the subject, dose intervals, administration routes, excretion rate, and combinations of NP and antibiotic(s) used. Any of the above dosage forms containing effective amounts are well within the bounds of routine experimentation and therefore, well within the scope of the instant present technology. By way of example only, such dosages may be used to administer effective amounts of the cationic peptide drug(s) to the patient and may include about 0.1 mg/kg, about 0.2 mg/kg, about 0.3 mg/kg, about 0.4 mg/kg, about 0.5 mg/kg, about 0.75 mg/kg, about 1 mg/kg, about 1.25 mg/kg, about 1.5 mg/kg, or a range between and including any two of the forgoing values. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once or twice per day, per 2 days, per 3 days, per week, per 10 days, per 2 weeks, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4 or more weeks.

In one aspect, the present nanoparticles are useful for the treatment of bacterial infections. The methods include administering to a subject suffering from a bacterial infection an effective amount of any NP (typically, but not necessarily loaded with an antibacterial drug) described herein. In any embodiment of the methods, the subject is infected by a drug-resistant bacterial strain and/or a bacterial biofilm. Both Gram-negative and Gram-positive bacterial infections may be treated, depending on the nature of the antibiotic incorporated into the NP. For example, in any embodiments, the subject may be infected with one or more of enterococcal or staphylococcal bacteria. In any embodiments, the subject may be infected with *pseudomonas* bacteria. In any embodiments, the subject may be infected with one or more of *E. coli, S. aureus* (including methicillin-resistant *S. aureus*, known as MRSA), and *P. aeruginosa*.

The examples herein are provided to illustrate advantages of the present technology and to further assist a person of ordinary skill in the art with preparing or using the NP of the present technology. To the extent that the compositions include ionizable components, salts such as pharmaceutically acceptable salts of such components may also be used. The examples herein are also presented in order to more fully illustrate certain aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Materials. 2,2'-Dithiodiethanol, acryloyl chloride, N-Boc-ethylenediamine and 1H-pyrazole-1-carboxamidine were purchased from Chem-Impex Int'l. Inc. (Wood Dale, IL, USA). 4-(Hydroxymethyl)phenylboronic acid pinacol ester and triphosgene were obtained from Acros Organics (Pittsburgh, PA, USA). Diethanolamine, diethylenetriamine and dextran were bought from Alfa Aesar (Tewksbury, MA, USA). Other reagents were purchased from Thermo Fisher Scientific (Fitchburg, WI, USA) and used as received unless otherwise stated.

Characterization. $^1$H NMR spectra of all intermediate and final polymer products were recorded on a Bruker 400 spectrometer in $CDCl_3$ at 25° C. The molecular weights (Mn and Mw) and polydispersity indices (PDI) of the polymers were determined by a gel permeation chromatographer (GPC) equipped with a refractive index detector, a light scattering detector, and a viscometer detector (Viscotek, USA). Dimethylformamide (DMF) with 10 mmol/L of LiBr was used as the mobile phase with a flow rate of 1 mL/min. The sizes and zeta potential of the NP were studied by dynamic light scattering (DLS, ZetaSizer Nano ZS90, Malvern Instruments, USA). The morphologies of the NP was visualized by transmission electron microscopy (TEM, Philips CM200 Ultra Twin) with phosphotungstic acid staining.

Example 1—Preparation of a Drug-Loaded Nanoparticle of the Present Technology

Synthesis of 2,2'-dithiodiethanol diacrylate. 2,2'-Dithiodiethanol (7.7 g, 50 mmol, 1.0 equiv) and triethylamine (TEA, 25 mL, 200 mmol, 4.0 equiv) were dissolved in 150 mL of anhydrous tetrahydrofuran (THF) in a 250 mL flask. This flask was immersed in an ice bath for 15 min, and then acryloyl chloride (11.3 g, 125 mmol, 2.5 equiv) was added dropwise to the stirred solution. The resulting heterogeneous solution was gradually warmed to room temperature and stirred for another 8 h, then filtered to remove TEA hydrochloride salt. The reaction mixture was concentrated by rotary evaporation and re-dissolved in 200 mL chloroform. This solution was washed sequentially three times with 100 mL each of 0.1 M $K_2CO_3$ and saturated NaCl aqueous solution. The crude product was concentrated in vacuo, and purified by column chromatography (Hex:EtAc=4:1). The final product was obtained as a colorless oil (with a yield of 84%) and stored in a freezer in the absence of light prior to use. $^1$H NMR in $CDCl_3$, δ ppm: 6.4 (d, 1H), 6.1 (q, 1H), 5.9 (d, 1H), 4.4 (t, 2H), 3.0 (t, 2H).

Synthesis of the PBAE-N-Boc polymer. 2,2'-Dithiodiethanol diacrylate 2.0 g (7.6 mmol), N-boc-ethylenediamine 1.22 g (7.6 mmol) and TEA 1.05 mL (7.6 mmol) were dissolved in 2 mL of anhydrous DMF. The mixture was stirred at 70° C. for 7 days in a nitrogen atmosphere. The product was purified by repeated precipitation in diethyl ether for three times and dried under vacuum. The PBAE-N-Boc polymer was obtained with a yield of 82%. $^1$H NMR in CDCl$_3$, δ ppm: 4.1-4.3 (4H), 3.6 (2H), 3.2 (2H), 2.9 (4H), 2.7 (4H), 2.5 (4H), 1.2 (9H).

Synthesis of the PBAE-G polymer. PBAE-N-Boc polymer (1.5 g, 4.1 mmol amine groups) was dissolved in a mixture of DCM and TFA solution (1:1, v/v, 15 mL) and stirred at RT for 1.5 h to remove the Boc group. After the reaction, all the solvent was removed by rotary evaporation. Thereafter, 4 mL anhydrous ethanol was added into the flask to dissolve the deprotected polymer. Subsequently, 1H-pyrazole-1-carboxamidine (1.32 g, 9.0 mmol) and 5.7 mL diisopropylethylamine (DIPEA, 32.6 mmol) was added. The resultant mixture was placed under nitrogen and stirred at 55° C. overnight. The product was precipitated in diethyl ether for three times and dried under vacuum to obtain yellow powder (yield 81%). $^1$H NMR in DMSO-d$_6$, δ ppm: 6.5-8.0 (3H), 4.1-4.3 (4H), 3.3 (4H), 3.0 (4H), 2.7 (4H), 2.5 (4H).

Synthesis of the PBAE-G-B-P polymer. Two drops of pyridine were added to triphosgene (0.57 g, 1.9 mmol) in anhydrous dichlormethane (DCM) solution (20 mL) to decompose triphosgene into phosgene. After stirring at room temperature for 20 min, the solution was cooled to 0° C. in an ice bath, and 4-(hydroxymethyl)phenylboronic acid pinacol ester (1.28 g, 5.5 mmol) dissolved in DCM (15 mL) was added dropwise. The reaction was stirred at room temperature for 8 h; subsequently the solvent and excess phosgene were removed by rotary evaporation, to obtain the product without further purification. The product was used freshly in the next step reaction.

The phenylboronic acid chloroformate obtained in the previous step was dissolved in 10 mL DCM and slowly added into a DCM solution containing PBAE-G polymer (0.34 g, 0.9 mmol guanidine groups) and DIPEA (1.48 g, 12 mmol). The reaction was stirred at room temperature for 8 h, then condensed by rotary evaporation and precipitated in diethyl ether for three times, to obtain the polymer with phenylboronic acid pinacol ester (PBAE-G-B-P) as yellow powder (yield 72%). $^1$H NMR in DMSO-d$_6$, δ ppm: 6.5-8.0 (3H), 7.7 (1.27H), 7.4 (1.27H), 5.1 (1.27H), 4.2 (4H), 3.6 (2H), 3.2 (2H), 3.0 (4H), 2.7 (4H), 2.5 (4H), 1.2 (12H).

The pinacol groups on the polymer were deprotected by diethanolamine via a transesterification procedure. The PBAE-G-B-P polymer (100 mg) was dissolved in a mixture of methanol and DMSO solution (9:1, v/v, 1 mL). Diethanolamine (13 mg, 0.13 mmol) was added into the solution and stirred at room temperature for 2 h. Two hundred microliters of 0.2 M HCl was then added to the solution and stirred for another 1 h. The product was purified by repeated precipitation in a mixed solution of acetone/diethyl ether for 4 times. After being dried completely in vacuum, the PBAE-G-B polymer without pinacol protection was obtained with a yield of 82%. $^1$H NMR in DMSO-d$_6$, δ ppm: 6.5-8.0 (3H), 7.8 (1.21H), 7.4 (1.21H), 5.2 (1.21H), 4.3 (4H), 3.4 (8H), 3.0 (8H). The molecular weight of the PBAE-G-B polymer was 9.9 kDa (PDI=1.38) measured by gel permeation chromatography (GPC). The PBAE-G-B polymer had a pKa of 6.1

Coupling PBAE-G-B with dextran. A mixture of PBAE-G-B polymer and dextran 40 at a series of ratios (1:0.1 to 1:1) were dissolved in anhydrous DMSO. TEA and molecular sieves were added to the solution and it was stirred at RT for 8 h. The reaction mixture was filtered to obtain the DMSO product solution.

To prepare the drug-loaded nanoparticle, 3.0 mg rifampicin was added to 300 μL of DMSO solution containing 30 mg polymer components. The mixture was slowly added into 1.5 mL PBS solution (pH 8.0) under vigorous stirring, and dialyzed (cut-off molecular weight, MWCO 3500 Da) in a PBS solution (pH 7.4) to remove the organic solvent and excess rifampicin. The empty nanoparticle was prepared following the same protocol, but without adding any drug. The sizes and zeta potentials of the NP with different polymer to dextran ratios were all characterized by dynamic light scattering (DLS) in a PBS solution. The particle size decreased gradually from 800 nm to 140 nm as the dextran to PBAE-G-B ratio increased from 0.1:1 to 0.7:1, and plateaued beyond 0.7:1. (FIG. 7) A dextran to PBAE-G-B ratio of 0.7:1 was used for the subsequent experiments.

Figure 2:
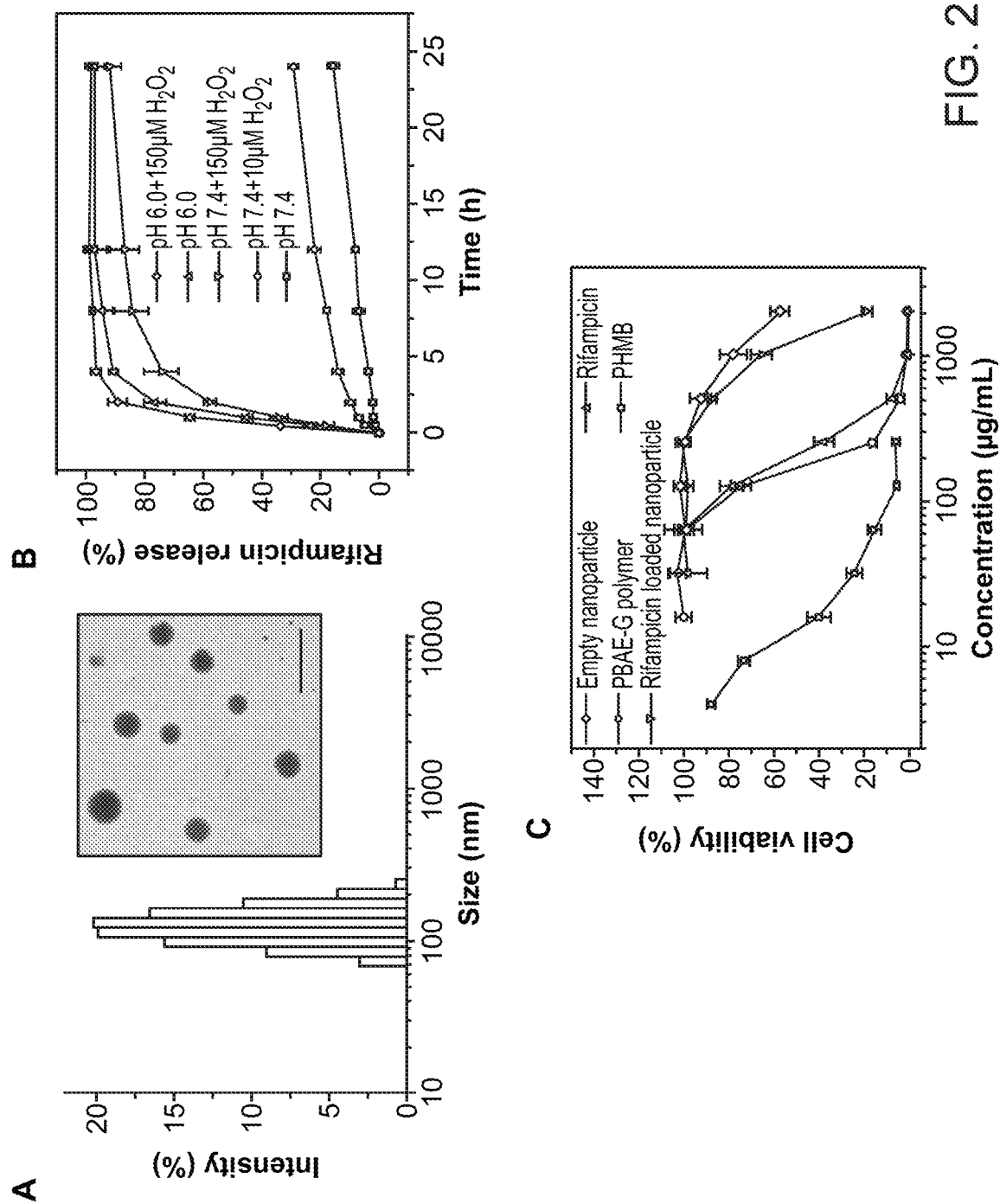
FIG. 2 shows data from an illustrative embodiment of the present technology: (A) Size and morphology of the NP characterized by DLS and TEM. Scale bar: 200 nm. (B) The rifampicin release profiles from the NP under different pH values and hydrogen peroxide levels. (C) Cytotoxicity assays of rifampicin, PBAE-G polymer and the NP with or without the encapsulation of the antibiotic, in RAW 264.7 murine macrophages. Poly(hexamethylene biguanide) (PHMB), a commercially available antimicrobial polymer is used as a positive control. (D) Hemolysis assay of red blood cells incubated with the PBAE-G polymer and the NP. (E-G) Checkerboard dilution assays performed on *P. aeruginosa*, which was used to evaluate the synergy between rifampicin and PBAE-G polymer (E), PBAE-G-B polymer at pH 6.0 (F), or PBAE-G-B polymer at pH 6.0 and with 150 μM $H_2O_2$ (G). The scale bars indicate the OD600 in each well 24 h after the treatment. (H, I) MIC of the PBAE-G polymer and the NP for *P. aeruginosa* (H, G−) and *M. smegmatis* (I, G+) under different conditions. (J) Zeta potential variations of *S. aureus* treated with NP under different pH and redox conditions.

The drug loading content and loading efficiency quantified by high performance liquid chromatography (HPLC) were 8.4% and 91.7%, respectively. The particle size and zeta potential of the drug-loaded NP as measured by Dynamic Light Scattering (DLS) were 139 nm and −13 mV, respectively. As shown in the transmission electron microscopy (TEM) images, the spherical drug-loaded NP had a relatively uniform size around 140 nm (FIG. 2A). FIG. 2B shows the drug release profile of the NP, demonstrating a clear stimuli-responsive characteristic. More than 70% of the drug was released within 4 h in the presence of either 150 μM $H_2O_2$ or low pH (i.e., pH 6.0). In contrast, less than 20% of the drug was released at the physiological condition (i.e., pH 7.4) after 24 h.

Example 2—Biological Methods

Bacterial strains. *S. aureus* Newman was kindly provided by Prof. Douglas Weibel; *E. coli* ATCC25922, *S. aureus* ATCC 33591 and *P. aeruginosa* ATCC 27853 were purchased from ATCC. *E. coli* DH5a was purchased from Thermo Fisher. These bacteria were grown in Mueller Hinton Broth (MHB) media (Criterion, Santa Maria, CA, USA). *M. smegmatis* mc$^2$155 strain was kindly provided by Prof. Adel M. Talaat's laboratory, and it was grown in Middlebrook 7H9 broth (HiMedia, West Chester, PA, USA).

Minimal inhibitory concentration (MIC) measurements. The MIC of the different treatments on various bacteria strains was determined using the Clinical Laboratory Standards Institute broth microdilution method[8]. Briefly, broth media (100 μL) containing two-fold serial dilutions of each compound were placed into a 96-well tissue culture plate. Each bacterial strain was taken from an exponentially growing culture and diluted to 5×10$^6$ CFU/mL. Ten microliters of such microbial suspension was inoculated in each well of the plate, resulting in a final bacteria concentration of approximately 5×10$^5$ CFU/mL. The bacteria were cultured at 37° C. for one day and their growth was observed by reading the optical density (OD) at 600 nm. The MIC was determined as the treatment concentration at which no microbial growth was observed. Broth containing microbial cells alone was used as a positive control and broth without bacteria inoculation was used as a negative control. Each test was carried out in 3 replicates.

Fractional inhibitory concentration (FIC) measurement. The synergy between the cationic polymer and antibiotic was assessed by checkerboard assays. The two antibacterial components were mixed in a 96-well plate with serial two-dimensional dilutions. Bacteria were inoculated in each well of the plate and their growth, reflected by the OD600 value, was monitored. The synergy effect was evaluated by calculating the FIC index according to the formula below:

$$FIC = \frac{MIC_A^{Comb}}{MIC_A} + \frac{MIC_B^{Comp}}{MIC_B}$$

$MIC_A^{Comb}$ and $MIC_B^{Comb}$ indicate the MICS of the two components in combination. The interactions between the two components are defined according to standard criteria of considering FIC≤0.5 as synergistic; 0.5<FIC≤1 as additive; 1<FIC≤4 as indifference; and FIC>4 as antagonism.

Cell viability test. Cytotoxicity of different NP components was tested using MTT assays. Raw 264.7 murine macrophage cells were seeded onto a 96-well plate (1×10⁴ cells/well) and cultured overnight. The cells were then treated with free antibiotic, PBAE-G polymer or NP with serial dilutions for one day and their viability was measured by a standard MTT assay. Data were collected by monitoring the difference between the absorbance at 560 nm and 650 nm using a GloMax-Multi Microplate Multimode Reader (Promega, WI, USA).

Hemolysis assay. Fresh mouse blood samples were purchased from BioIVT Elevating Science and the blood cells were collected using a centrifuge at 5000 rpm for 5 min, washed with PBS buffer for 3 times and suspended in PBS to a final concentration of approximately 4% (v/v). The antimicrobial polymer and the NP were serial diluted with PBS and placed in 96-well plates (100 μL/well). The blood cell suspension (10 μL/well) was added into the wells and incubated at 37° C. for 1 h to allow the complete hemolysis process. PBS and deionized water containing 1% Triton X-100 were used as negative and positive controls, respectively. Following centrifugation at 3000 rpm for 7 min, the supernatant (70 μL/well) was transferred to another clean 96-well plate. OD 560 in each well was monitored by a microplate reader, and hemolysis was calculated using the following formula:

$$\text{Hemolysis (\%)} = \frac{OD\ 560_{Sample} - OD\ 560_{PBS}}{OD\ 560_{Triton} - OD\ 560_{PBS}} \times 100\%$$

Rifampicin release kinetics. The nanoparticle was dispersed in PBS solution (1 mL, 10 mg/mL) with different pH (pH 6.0, 7.4) and hydrogen peroxide (0, 10 μM and 150 μM) levels, then sealed in dialysis bags (MWCO 3500 Da) and immersed in 40 mL PBS buffer with the corresponding conditions. The dialysis systems were incubated in a 37° C. shaker and 100 μL samples outside the dialysis bag were collected at different time intervals for HPLC analysis.

Bacterial Zeta Potential Measurements

Exponentially growing bacteria (*S. aureus* Newman) was collected by centrifugation at 8000 rpm for 5 min, washed with saline and diluted to OD 600 value of 0.1. The bacterial solution was incubated with the NP under different pH and redox conditions at 37° C. for 2 h. After incubation, the unbound NP was removed by centrifugation (8000 rpm, 4 min). The obtained pellets were washed once and re-suspended with 0.5 mL PBS for DLS test.

NP and bacteria colocalization assay. To observe the colocalization of different components of the NP with bacteria, dextran and PBAE-G polymer were labeled with Cy5.5, and rifampicin was reacted with rhodamine B isothiocyanate to obtain rif-rho. The NP applied in this experiment was composed of dextran-Cy5.5, unlabeled PBAE-G-B polymer and rif-rho. Exponentially growing bacteria (MRSA ATCC 33591 and *P. aeruginosa* ATCC 27853) were collected by centrifugation at 8000 rpm for 5 min, washed with saline and diluted to OD 600 value of 0.5. The bacteria suspensions were incubated with mixed stains containing acridine orange (10 μg/mL), free rif-rho (1.6 μg/mL), NP with an equivalent amount of rif-rho, free dextran-Cy5.5 (7.6 μg/mL) or free PBAE-G-Cy5.5 (10.8 μg/mL), at different pH and redox conditions for 1 h. After washing with saline two times, the bacteria were resuspended in 70% glycerol and observed by confocal laser scanning microscope (CLSM, Nikon Eclipse Ti, Japan).[3]

AO/PI bacterial staining assay. Exponentially growing bacteria (*P. aeruginosa* ATCC 27853 and MRSA ATCC 33591) were collected by centrifugation at 8000 rpm for 5 min, washed with saline and diluted to OD 600 value of 0.5. The bacterial suspensions were incubated with different treatments at 37° C. for 1 h, and then washed with saline and stained with acridine orange (10 μg/mL) and propidium iodide (PI, 5 μg/mL) simultaneously for fifteen minutes. Afterward, the bacteria were collected via centrifugation, washed with saline twice, resuspended in 70% glycerol and spread on glass slides. The bacteria were observed using CLSM.

Scanning electron microscopy (SEM) observation. Bacteria suspensions were prepared as above and treated with NP at different pH or redox conditions for 2 h, washed with saline and fixed with 2.5% glutaraldehyde at 4° C. overnight. The samples were washed with Milli-Q water and dehydrated with a series of graded ethanol solutions (50%, 75%, 90%, 100%, each for 5 min). After one day drying, the samples were coated with platinum and observed by SEM (Zeiss/LEO 1530).

Biofilm inhibition assays. Exponentially growing bacteria were inoculated into 96 well plates (1×10⁴ cell/well) containing MHB broth with 2% (w/v) glucose, and incubated under stationary conditions at 37° C. for one day. After biofilm formation, the medium was discarded, and the plates were washed with PBS to remove the planktonic bacteria. Fresh MHB broth containing serially diluted free rifampicin or NP was added to the plates and incubated at 37° C. for another 24 h. The media in each well was then removed, and the plates were washed carefully with PBS one time. The biofilm in each well was fixed with 95% ethanol for 15 min and stained with 0.1% crystal violet for 15 min. After the biofilm was washed with Milli-Q water for three times, 33% v/v acetic acid (100 μL/well) was added to the plate to solubilize the crystal violet staining. OD 560 in each well was read to assess the biofilm formation.

To observe the biofilm accumulation and penetration capability of the NP, MRSA biofilm was grown in a glass-bottom petri dish for one day. The biofilm was stained with a mixture of AO (10 μg/mL) and free rif-rho (1.6 μg/mL), NP with an equivalent amount of rif-rho or free Cy5.5-labeled dextran (7.6 μg/mL) for 15 or 45 min. The biofilm was then washed with saline twice and monitored by CLSM.

Evaluation of antibiotic resistance development. *E. coli* ATCC 25922 was employed to study drug resistance development under sublethal dose treatments of free rifampicin, PBAE-G polymer or the NP. Bacteria were seeded in EP tubes containing 1 mL media (1×10⁶ CFU/tube) with a serially diluted free antibiotic, PBAE-G polymer, or NP, and passaged every 24 h. The OD 600 value in each tube was examined to determine the MIC, and the bacteria cultured in the tube containing rifampicin at a ½ MIC was used for passage. The MIC for each passage was recorded and compared to that of the first passage to determine the drug resistance enhancement.

ROS level measurement in Raw 264.7 cells. Raw 264.7 cells were seeded in a 96-well plate at a density of $1.5\times10^4$ cells per well and cultured overnight. The cells were incubated in the culture media with or without LPS (1 µg/mL) for 16 h, and then treated with 10 µM DCFH-DA probe for 15 min. After the removal of excessive DCFH-DA, the cells were washed twice with PBS and the fluorescence intensity of 2,7-dichlorofluorescein (DCF) was analyzed using flow cytometry.

Intracellular rifampicin uptake and subcellular distribution test. Raw 264.7 cells were seeded in a 96-well plate at a density of $1.5\times10^4$ cells per well, cultured overnight and pretreated with LPS (1 µg/mL) for 16 h. The cells were incubated with rif-rho (25 µM) or NP with an equivalent amount of rif-rho for 1 h. The cells were washed twice with PBS, harvested, and the intracellular rhodamine fluorescence was monitored using flow cytometry.

To measure the subcellular NP and rif-rho distribution, Raw 264.7 cells were seeded in a glass-bottom petri dish at a density of $3\times10^5$ cells per dish and cultured overnight. The cells were incubated in the culture media with or without LPS (1 µg/mL) for 16 h. The cells were then further incubated with rif-rho (25 µg/mL) or Cy5.5 labeled NP with an equivalent amount of rif-rho at 37° C. for 30 min or 2 h, and then washed with PBS twice. The nuclei and lysosomes of the cells were stained with Hoechst 33342 and Lysotracker green for 30 min, and observed using CLSM.

Antimicrobial activity for intracellular infection. The antimicrobial activity for intracellular infection was tested following a previous report[41]. Briefly, macrophage Raw 264.7 cells were seeded in 96-well plate at a density of $1\times10^4$ cells/well overnight and infected with MRSA or *P. aeruginosa* at a ratio of 10-20 bacteria per macrophage in FBS free RPMI 1640 medium. After 2 h of incubation, the cells were washed and cultured in 1640 medium containing 10% FBS and 50 µg/mL gentamicin for 8 h to prevent the growth of extracellular bacteria. Then the macrophages were treated with free rifampicin or the NP with an equivalent amount of rifampicin for one day and lysed with Milli-Q water supplemented with 0.1% Triton-X. The cell lysates were serially diluted and the CFU in each well was determined by plating on MHB agar plates.

Biosafety and Ethics

All of the experiments were performed following the biosafety protocol and the animal protocol approved by the Institutional Animal Care and Use Committee (IACUC) at the University of Wisconsin-Madison.

In vivo imaging of MRSA infection. The targeting ability of the NP to the MRSA infection site was investigated through in vivo imaging. The lower body of the ICR mice (female, 22-24 g, Charles River, n=3) was shaved and the right thigh was infected with MRSA ($5\times10^6$ CFU/mouse) one day before imaging. Cy5.5 labeled NP was administrated through i.v. injection and the fluorescence images were captured through an in vivo imaging system (IVIS) at scheduled time points (0, 0.5, 1, 2, 4, 8, 24 h post-injection). For ex vivo imaging, the mice were sacrificed at 24 h after injection and the major organs including heart, kidneys, spleen, lung, liver and both thighs were excised, washed with 0.9% saline and imaged.

Mouse lung infection model. Six-week-old, specific-pathogen-free, female ICR/Swiss mice weighing 23 to 27 g were used for the lung infection experiment. The mice were immunosuppressed with two subcutaneous (s.c.) injections of cyclophosphamide at four days (150 mg/kg) and one day (100 mg/kg) prior to the infection. At day 0, *P. aeruginosa* (ATCC 27853, $5\times10^8$ CFU per mouse) was inoculated into the lungs via nasal inhalation, and the infected mice were randomly divided into 4 groups (n=3 per group). Two hours after the infection, a single dose of different treatment groups was given through i.v. injection. Twenty-four hours after the inoculation, the animals were euthanized by $CO_2$ asphyxiation and their lungs were harvested and homogenized for CFU determination.

Mouse peritonitis model. ICR mice (female, 22-24 g, Charles River) were immunosuppressed by cyclophosphamide as described above. At day 0, MRSA ATCC 33591 ($1\times10^8$ CFU/mL in saline, 0.1 mL bacteria suspension per injection) was inoculated via the i.p. route, and the infected mice were randomly divided into 4 groups (n=6). One hour after the infection, a single dose of the treatment at a dose of 5 mg/kg was given through i.v. injection. Twelve hours after the inoculation, the animals were euthanized by $CO_2$ asphyxiation and their organs (kidneys, liver, spleen, lung) and ascites were collected. To collect the ascites sample, 3 mL PBS was given through i.p. injection, and the abdomens of the mice were gently massaged. Peritoneal fluid was then removed from the peritoneum by syringe. The organs and tissue were homogenized and CFU was determined by serial dilution and plating.

Histopathological analysis. Healthy ICR mice were randomly divided into 4 groups (n=3 per group) and treated with either saline, free rifampicin, empty NP and rifampicin-loaded NP, with an equivalent dose of 5 mg/kg rifampicin once a day for three days via the intravenous route. On day four, blood was drawn from orbital sinus for blood biochemistry testing (VETSCAN® VS2 Chemistry Analyzer), and the mice were euthanized. The main organs including lung, heart, liver, spleen and kidneys were collected, sectioned using a freezing microtome and stained with hematoxylin and eosin (H&E) for histological examinations.

Statistical analysis. Results are presented as mean±standard deviation. Assignments of the mice to treatments and selections of fields of microscopic inspection were made at random. Differences between the experimental groups were assessed using a one-way ANOVA test followed by Tukey's post hoc comparison test. Analyses were performed using a GraphPad Prism software. Significant differences between groups were indicated by * $p<0.05$,  $p<0.01$, * $p<0.001$, respectively. $p<0.05$ was considered to be statistically significant in all analyses (95% confidence level).

Example 3—Biological Results and Discussion

Biosafety evaluation of the NP. The cytotoxicities of rifampicin, the PBAE-G polymer and the NP on Raw 264.7 murine macrophage cells were tested via an MTT assay. As shown in FIG. 2C, rifampicin and the PBAE-G polymer exhibited similar cytotoxicity on Raw cells, with a half maximal inhibitory concentration (IC50) of 210 and 172 µg/mL, respectively. Compared with the cationic PBAE-G polymer, the dextran coating of the NP significantly improved the biocompatibility of empty NP with an IC50 higher than 2000 µg/mL. The IC50 of rifampicin-loaded NP was 1297 µg/mL, which is 6-7 times higher than that of free rifampicin and PBAE-G polymer, and is more than 100 times higher than that of the positive control polyhexanide (PHMB), a commercially available cationic polymer that is widely used as a broad-spectrum antiseptic. Moreover, neither the PBAE-G polymer nor the NP showed hemolytic activity in mouse red blood cells at a high concentration of 2048 µg/mL, indicating good biocompatibility in blood (FIG. 2D).

In vitro antimicrobial efficacy of the NP. The synergy of the PBAE-G polymer and rifampicin against two rifampicin-resistant strains, P. aeruginosa (ATCC 27853, Gram-negative, G−) and M. smegmatis (mc² 155, Gram-positive, G⁺), were investigated (Table 1). The fractional inhibitory concentrations (FICs) of rifampicin were significantly reduced in the presence of a low dose of the PBAE-G or PBAE-G-B polymer FIGS. 2E-G). The FIC indexes between rifampicin and the PBAE-G-B polymer in a low pH and high ROS condition were 0.188 and 0.25, for P. aeruginosa and M. smegmatis, respectively, indicating synergy.

TABLE 1

Antimicrobial activity of various antibiotics and their synergy with the PBAE-G polymer against MRSA and P. aeruginosa.

|  |  | MRSA |  | P. aeruginosa |  |
| --- | --- | --- | --- | --- | --- |
| Antibiotic | Class | MIC | FIC index | MIC | FIC index |
| Rifampicin | Rifamycin | 0.016 | 1 | 32 | 0.25 |
| Ciprofloxacin | Quinolone | 0.5 | 2 | 0.25 | 1 |

TABLE 1-continued

Antimicrobial activity of various antibiotics and their synergy with the PBAE-G polymer against MRSA and P. aeruginosa.

|  |  | MRSA |  | P. aeruginosa |  |
| --- | --- | --- | --- | --- | --- |
| Antibiotic | Class | MIC | FIC index | MIC | FIC index |
| Vancomycin | Glycopeptide | 1 | 1 | 1024 | 2 |
| Clindamycin | Lincosamide | 32 | 0.562 | >1024 | <0.25 |
| Streptomycin | Aminoglycoside | 16 | 0.266 | 16 | 0.25 |
| Gentamicin | Aminoglycoside | 1 | 0.5 | 1 | 0.375 |
| Amoxicillin | β-lactam | 128 | 0.75 | 1024 | 2 |

The in vitro antimicrobial activity of the NP was evaluated under different pH and redox conditions, which mimicked the normal physiological condition and the microenvironment of infected tissues. As expected, the NP exhibited a significantly lower minimum inhibitory concentrations (MIC) under acidic pH or in the presence of 150 μM $H_2O_2$, since the stimuli triggered the destabilization of the NP and the subsequent release of antimicrobial compounds (i.e., the cationic polymer and rifampicin). The MIC of the NP for M. smegmatis was 16 μg/mL under an oxidizing environment, which is 8 folds lower than that of free rifampicin (128 μg/mL), indicating a high potency in eliminating AMR microbes (FIGS. 2H, 2I). The NP exhibited a lower MIC in oxidizing environment than in acidic pH, attributed to the higher bactericidal activity of the PBAE-G polymer than its phenylboronic acid modified counterpart PBAE-G-B. The antimicrobial property of the cationic polymers and the NP against a broad spectrum of bacteria were tested and the results are shown in Table 2. The therapeutic index (the value of IC50 versus MIC) of the NP on P. aeruginosa and M. smegmatis was 41 and 81, respectively; while the therapeutic index of free rifampicin for these two strains was 6.5 and 1.6, respectively. A higher therapeutic index means a higher selectivity for killing bacteria than killing mammalian cells[1]. The considerably higher therapeutic index of the NP over free antibiotic indicates the selective bactericidal ability of NP toward the AMR pathogens over mammalian cells. Notably, the NP did not show enhanced benefit in treating S. aureus (Newman) and MRSA since these two strains are sensitive to rifampicin and are suppressed under low dose of free antibiotic.

TABLE 2

Biological properties of the polymers and the NP.

|  | MIC (μg/mL) | | | | | | RAW 264.7 IC50 (μg/mL) |
| --- | --- | --- | --- | --- | --- | --- | --- |
|  | E. coli (DH5 alpha) | E. coli (ATCC 25922) | S. aureus (Newman) | MRSA (ATCC 33591) | P. aeruginosa (ATCC 27853) | M. smegmatis (MC² 155) |  |
| Rifampicin | 16 | 16 | 0.016 | 0.016 | 32 | 128 | 210 |
| PBAE-G polymer | 64 | 64 | 32 | 32 | 128 | 32 | 172 |
| PBAE-G-B pH 6.0 | 128 | 128 | 64 | 64 | 256 | 64 | — |
| PBAE-G-B pH 6.0 + 150 μM $H_2O_2$ | 64 | 64 | 32 | 32 | 128 | 32 | — |
| NP | 128 | 128 | 1 | 2 | 256 | 128 | 1297 |
| NP pH 6.0 | 32 | 32 | 0.25 | 0.25 | 64 | 32 | — |
| NP 150 μM $H_2O_2$ | 16 | 16 | 0.25 | 0.25 | 32 | 16 | — |
| PHMB | 10 | 10 | 10 | 10 | 40 | 10 | 11.9 |

The numbers in brackets are the FICs of rifampicin.

To evaluate the stimuli-triggered NP destabilization and activation, the count rates of the NPs in an aqueous solution under different pH/ROS conditions were measured by DLS. The count rate reflects the NP concentration present in the sample solution. As shown in FIG. 8, the count rate of the NP was stable at pH 7.4, but decreased in the presence of the stimuli. Low pH led to a quicker drop in the count rate, indicating a higher sensitivity of the NP to the acidic environment than to ROS. Under both low pH and high ROS, a faster NP destabilization was observed than with low pH or high ROS alone. To further assess the interactions of the activated NP with the microbes, S. aureus was incubated with NP under different pH and redox conditions and the change of zeta potential was monitored. As shown in FIG. 2J, the zeta potential changed from −12 mV to 9 or 6 mV under 150 μM $H_2O_2$ or pH 6.0, respectively, confirming a charge reversal of the PBAE-G-B polymer triggered by either $H_2O_2$ or acidic pH. After the PBAE-G-B polymer restored the positive charge and was released from the NP, it exhibited a strong electrostatic adherence to the negatively charged bacterial surface.

Serum stability is also an important parameter for the in vivo application of antimicrobial agents. We investigated whether serum protein could affect the antimicrobial activity of the NP. Pre-incubation of the NP with serum-containing media at 37° C. for 24 h did not affect its efficacy in treating *E. coli* and *M. smegmatis* as evidenced by similar MICs to those of the non-serum control groups. Similarly, for *P. aeruginosa*, the NP was stable in serum-containing media for 16 h. However, the MIC for *P. aeruginosa* increased 2-fold after 24 h pre-incubation.

Figure 3:
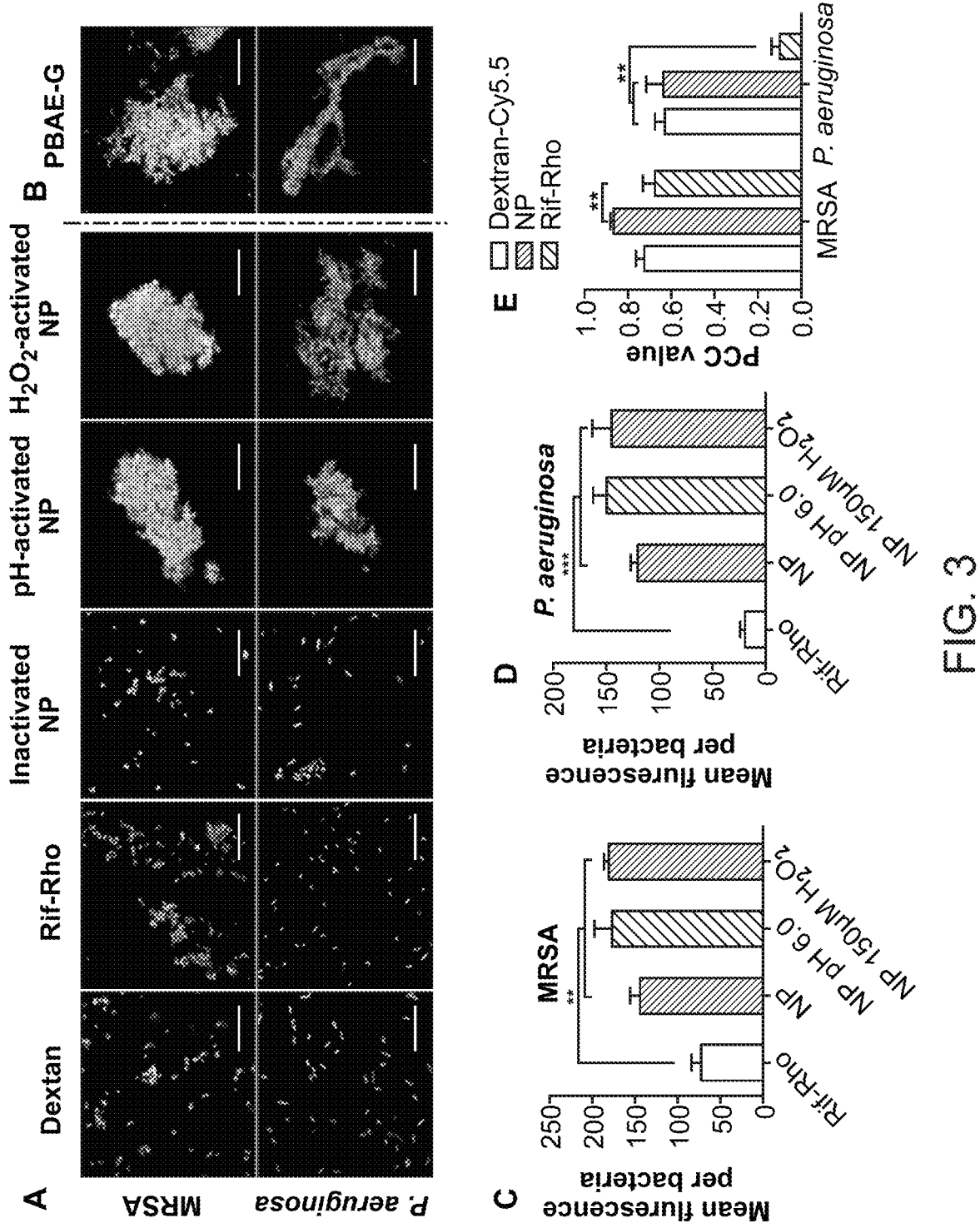
FIG. 3 shows data from an illustrative embodiment of the present technology: (A) Colocalization study of the NP and bacteria, monitored by confocal laser scanning microscopy (CLSM). Fluorophore Cy5.5 labeled dextran (dextran-Cy5.5, blue) was used to construct the NP; rhodamine B isothiocyanate tagged rifampicin antibiotic (Rif-Rho, red)
Figure 3:
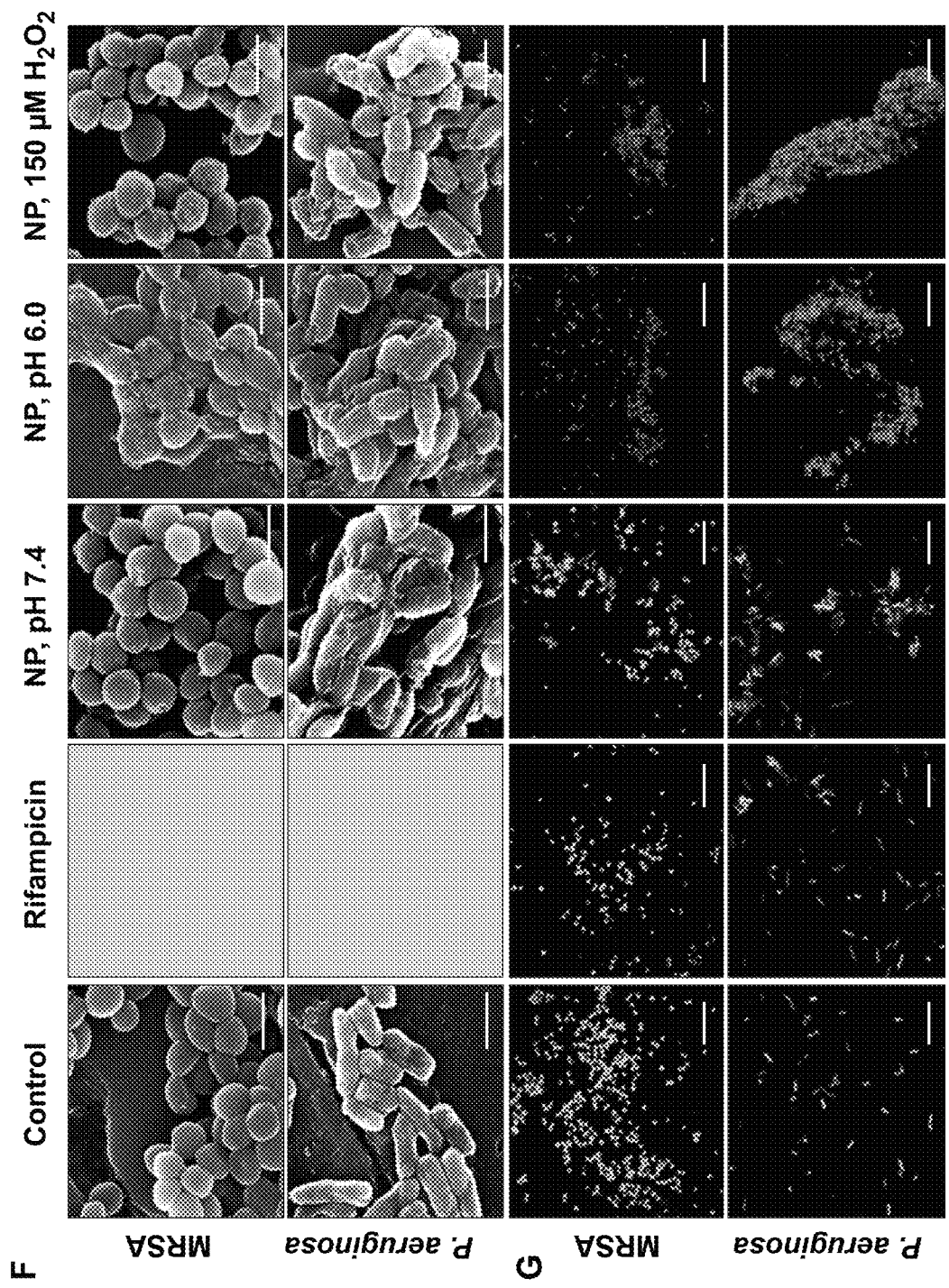

To illustrate the interactions between the NP and bacteria and investigate the underlining mechanisms of mitigating AMR, confocal laser scanning microscopy (CLSM) was employed to study the colocalization of the NP and bacteria. Dextran, coated on the NP surface, was labeled with Cy5.5 fluorophore (blue) to track the distribution of the NP. Rifampicin was conjugated with rhodamine B isothiocyanate to yield rifampicin-rhodamine (rif-rho, red). The bacteria were stained with acridine orange (AO, green) and then incubated with the dye-labeled NP and its components (i.e., Cy5.5-labeled dextran and rif-rho) under different pH and redox conditions. A rifampicin sensitive strain MRSA (ATCC 33591, $G^+$) and a rifampicin resistant strain *P. aeruginosa* (ATCC 27853, $G-$) were tested and the results are shown in FIGS. 3A, 3B. In the free rif-rho-treated group, a moderate red fluorescence signal of rif-rho was evenly distributed in MRSA, but was barely observed in *P. aeruginosa*, which is consistent with the degrees of resistance associated with the two strains. Different from the free antibiotic, in the Cy5.5-labeled dextran treated group, an overlap of blue and green signals was found in both strains, demonstrating a strong affinity of dextran with bacterial surface. The NP with dextran coating showed a similar bacteria-binding ability as the free dextran. The accumulation of NP in both strains was demonstrated by the white color shown in the image, which is generated by the colocalization of all three fluorescence signals. The bacteria incubated with stimuli (pH 6.0 or 150 μM $H_2O_2$)-activated NP also displayed strong overlapped of all three fluorescence signals. In contrast to inactivated NP-treated groups that displayed well dispersed bacteria, the bacteria in the activated NP-treated groups aggregated to form bacterial clusters due to the interactions between the cationic polymers released from the NP and the bacteria. Such an agglomeration caused by the bacteria and the cationic polymers released initially by a fraction of the NPs shaped a microenvironment entrapping a high level of the drug locally, thus leading to an improved antimicrobial capacity. As shown in FIG. 3B, Cy5.5-labeled free PBAE-G polymer also induced bacteria aggregation, a further indication of the strong affinity between the cationic polymer and the bacteria. The rhodamine fluorescence intensity in all of the NP-treated groups was significantly higher than that of the free rif-rho-treated group, especially for drug-resistant *P. aeruginosa*, indicating a much higher drug accumulation in bacteria induced by the NP (FIGS. 3C, 3D). This observation was supported by Pearson's correlation coefficient (PCC) that quantifies the colocalization degree of two colors (FIG. 3E). The overlap of *P. aeruginosa* with Cy5.5-labeled dextran and/or NP was significantly higher than that with free rif-rho, suggesting a dextran induced drug accumulation.

To further investigate the interactions between the NP and the bacteria, MRSA and *P. aeruginosa* were incubated with the NP under different pH and redox conditions and observed through scanning electron microscopy (SEM) (FIG. 3F). Under a physiological condition (pH 7.4), the attachment of NP on the bacterial surface can be clearly seen, denoted by green arrows, which was consistent with the previous colocalization results and verified the efficient binding and adhesion of the NP with the bacteria. Membrane disruption and deformation were observed on the bacteria treated with NP in the presence of 150 μM $H_2O_2$ or low pH. Compared with the clear and smooth boundary exhibited by the bacteria in the control group, the holes on the bacterial surfaces induced by the cationic polymers in the NP treated groups indicated an increased permeability and thus attenuated drug resistance.

The damage of the bacteria envelope was further explored by an AO/PI staining assay[2]. As shown in FIG. 3G, neither rifampicin nor inactivated NP enhanced bacterial membrane permeability. In contrast, both low pH- and $H_2O_2$-activated NP led to significant red signal in both bacterial strains. The AO/PI staining results substantiated the release of the cationic polymer upon NP activation and their ability to disturb bacterial membrane, enabling the penetration of small molecules such as PI or antimicrobial drugs.

Antibiofilm activity of the NP. The antibiofilm activity of the NP on both $G^+$ and $G^-$ strains was evaluated by crystal violet staining assay (FIGS. 4A-C). Although planktonic MRSA microbes ($G^+$) are sensitive to rifampicin, its biofilm displayed enhanced resistance. More than 80% biofilm remained after the free rifampicin treatment (32 μg/mL). Similarly limited efficacy of free rifampicin was also observed in $G^-$ strains (i.e., *P. aeruginosa* and *E. coli*). Both pH- or ROS-activated NPs significantly sensitized the antibiotic in the biofilm state resulting in elimination of more than 90% or 95% biofilms for all three strains at a rifampicin concentration of 16 and 32 μg/mL, respectively. The inactivated NP had a moderate anti-biofilm capacity that fell in between the free antibiotic and the activated NP.

To explore the potential anti-biofilm mechanism of the NP, MRSA biofilm was incubated with fluorescence probe-labeled NP (made by Cy5.5-labeled dextran and loaded with rif-rho) and observed by CLSM with a z-stack image. As shown in FIG. 4D, strong red fluorescence signal was observed on the surface of biofilm in the free rif-rho-treated group, indicating the surface retention and limited penetration of the free drug. The NP with hydrophilic dextran coating exhibits limited low interaction with extracellular polymeric substances (EPS), which facilitated NP penetration in biofilm. For the inactivated NP-treated group, strong purple signals (a mixture of red and blue signals) were observed in the deep layers of the biofilm at 45 min, suggesting an extensive biofilm penetration and accumulation. pH- and ROS-activated NPs exhibited higher NP accumulation and more extensive NP penetration in the biofilm than inactivated NP. This observation may be attributed to the fact that the stimuli-induced cationic polymers interact strongly with the negatively charged EPS.

The cationic polymer could also disrupt and decompose the EPS network, thus improving the dispersion of the antibiotic in biofilm and enhancing the anti-biofilm efficacy[4]. Forty-five minutes post-treatment, the payload drug in stimuli-activated NPs were released in situ in the biofilm, and its red fluorescence was evenly distributed throughout the biofilm. The stimuli-responsive drug release profile was semi-quantitatively determined by the significantly reduced PCCs between the Cy5.5 labeled NP and rif-rho in both low pH and ROS treated biofilm groups (FIG. 9A). The PCCs between the bacteria and the antibiotic for activated NPs were significantly higher than that for the inactivated NP, which implied that the released drug could successfully reach the bacteria (FIG. 9B). However, the PCCs between the bacteria and dextran were low in all of the treatment groups (FIG. 9C). While dextran showed a strong binding with planktonic microbes (FIG. 3A), it did not bind the bacteria in the biofilm, presumably because the lectins on the bacterial surface were already saturated by the extracellular polysaccharides in the biofilm. The normalized drug fluorescence intensity versus biofilm depth was quantitatively described in FIG. 4E, 4F, and the total rif-rho fluorescence intensity accumulated in the biofilm was calculated and shown in FIG. 4G. The pH- and ROS-activated NPs showed the highest drug accumulation in the biofilm, which is consistent with their antibiofilm performances.

Elimination of intracellular infections. Eliminating intracellular infection is essential in the treatment of infectious diseases since pathogens persisting in macrophages elude antibiotic attack, leading to relapsing and refractory infections. Dextran coated on the surface of the NP can target macrophages and induce selective internalization, conferring the NP with the ability to treat intracellular infections[5]. However, pathogens in macrophages mainly reside in cytosol, thus requiring the NP to escape the endosome and release the payload in the cytosol. FIGS. 5A and 5B show uptake and subcellular trafficking of NP in Raw 264.7 macrophages with or without LPS pretreatment. Raw 264.7 macrophages exhibited a high intracellular NP accumulation under both conditions due to the expression of C-Type lectins on the cell surface. The LPS-stimulated macrophages had a higher level of intracellular ROS compared with normal cells, which accelerates NP activation and cytosolic release of rif-rho (FIG. 5C). The quantitative analysis of the cellular uptake of rif-rho in LPS-stimulated macrophages was further investigated by flow cytometry (FIG. 5D). The NP significantly enhanced intracellular drug accumulation due to dextran-mediated interaction with macrophages, compared with the free drug that entered the cell through passive diffusion.

The effectiveness of the NP in eliminating intracellular infections was studied in macrophages infected with *S. aureus* or *P. aeruginosa* (FIGS. 5F-5H). Compared with the planktonic ones, the intracellular pathogens exhibited much higher resistance to the antibiotic, which was in correspondence with previous reports[6]. The NP significantly improved the antimicrobial efficacy against intracellular bacteria in comparison with free rifampicin, which was likely due to the higher drug level in the cytosol.

Prevention of antimicrobial resistance (AMR) development. Continuous use of antibiotics can drive the selection of drug-resistant pathogens[7]. To investigate the level of AMR development induced by the NP, *E. coli* was incubated with a sub-lethal dose of free rifampicin, NP, and PBAE-G polymer (0.5 MIC) for 20 passages (FIG. 5I). In the free rifampicin-treated group, the MIC gradually increased from passage 3 and reached 40-fold after 20 passages, suggesting the high resistance of *E. coli* to free rifampicin. By contrast, the NP and the polymer only led to mild and delayed resistance. The bacteria incubated with the NP exhibited only a two-fold increase in MIC after 16 passages, suggesting a low risk of developing resistance.

In vivo biodistribution. We next explored the in vivo distribution of the Cy5.5-labeled NP in mice with MRSA thigh infection. The Cy5.5-labeled NP accumulated in the infected thigh 1 h post-injection and peaked at 8 h. The semi-quantitative analysis of the fluorescence image showed a 6.6 times difference between the two thighs at 8 h post-injection (FIGS. 6A-6D). The mice were sacrificed after 24 h and the major organs and tissues were collected for ex vivo imaging. According to FIG. 6E, except liver, an organ responsible for detoxification in the body, the infected thigh showed the highest fluorescence intensity, demonstrating the targeting capability of the NP to the infected tissues.

In vivo antimicrobial efficacy. The in vivo antimicrobial efficacy of the NP was evaluated in the *P. aeruginosa* pneumonia and MRSA induced peritonitis models. For the pneumonia model, ICR mice were rendered neutropenic by cyclophosphamide administration and inoculated with 5×10$^8$ CFU *P. aeruginosa* through intranasal administration to mimic hospital-acquired pneumonia, and then treated with different formulations (5 mg/kg rifampicin, or an equivalent dose of the NPs) via i.v. injection (FIGS. 6F and 6G). The rifampicin-loaded NP exhibited the highest antimicrobial efficacy among the three treatment groups and led to more than four orders reduction in CFU. Empty NP also revealed moderate efficacy resulting in a nearly two order reduction in CFU. In contrast, free rifampicin showed a very limited efficacy due to the strong drug resistance of *P. aeruginosa*.

For the peritonitis model, different treatments were administered by the intravenous route 1 h after the infection, and the CFU in the various organs were determined 12 h after the infection (FIGS. 6H-6M). The rifampicin-loaded NP significantly enhanced the therapeutic efficacy compared with free rifampicin and the empty NP, and eliminated >99.9% pathogens in all of the organs tested.

Healthy mice subjected to three daily NP administrations via intravenous route (containing 5 mg/kg rifampicin for each injection) did not show any significant variations in blood biochemical parameters including alanine aminotransferase, aspartate aminotransferase, alkaline phosphatase, creatinine, blood urea nitrogen, total bilirubin, glucose, total protein, globulin, albumin, sodium ion and potassium ion, indicating its low systemic toxicity towards liver and kidney. Tissue histology analysis also proved the high biosafety of the NP, since no observable toxicity-related damage was seen in any of the major organs after NP treatment.

REFERENCES

1. Muller P Y, Milton M N. The determination and interpretation of the therapeutic index in drug development. *Nature reviews Drug discovery* 2012, 11(10): 751-761.
2. Xu H, Fang Z, Tian W, Wang Y, Ye Q, Zhang L, et al. Green fabrication of amphiphilic quaternized β-chitin derivatives with excellent biocompatibility and antibacterial activities for wound healing. *Advanced Materials* 2018, 30(29): 1801100.
3. Lawrence J, Wolfaardt G, Korber D. Determination of diffusion coefficients in biofilms by confocal laser microscopy. *Applied and environmental microbiology* 1994, 60(4): 1166-1173.
4. Chung P Y, Khanum R. Antimicrobial peptides as potential anti-biofilm agents against multidrug-resistant bacteria. *Journal of microbiology, immunology and infection* 2017, 50(4): 405-410.
5. Pustylnikov S, Sagar D, Jain P, Khan Z K. Targeting the C-type lectins-mediated host-pathogen interactions with dextran. *Journal of pharmacy & pharmaceutical sciences: a publication of the Canadian Society for Pharmaceutical Sciences, Societe canadienne des sciences pharmaceutiques* 2014, 17(3): 371.
6. Lehar S M, Pillow T, Xu M, Staben L, Kajihara K K, Vandlen R, et al. Novel antibody-antibiotic conjugate eliminates intracellular *S. aureus*. *Nature* 2015, 527 (7578): 323.
7. Brandis G, Wrande M, Liljas L, Hughes D. Fitness-compensatory mutations in rifampicin-resistant RNA polymerase. *Molecular microbiology* 2012, 85(1): 142-151.

8. Clinical, Institute L S. Methods for dilution antimicrobial susceptibility tests for bacteria that grow aerobically; approved standard. Clinical and Laboratory Standards Institute Wayne, PA; 2012.

EQUIVALENTS

While certain embodiments have been illustrated and described, a person with ordinary skill in the art, after reading the foregoing specification, can effect changes, substitutions of equivalents and other types of alterations to the NPs of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified. Moreover, use of any of the foregoing terms in the description with respect to a particular element or embodiment also contemplates the use of any of the other terms. For example, use of "comprise" with respect to one element or embodiment will also be understood to disclose use of "consisting essentially of" or "consists of" in respect of the same element or embodiment and vice versa.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:
1. A nanoparticle comprising:
   a surface comprising one or more polysaccharides having specific binding affinity for bacteria;
   a core comprising a biodegradable polymer; and
     an antibacterial drug loaded within the core;
   wherein the biodegradable polymer comprises a repeating subunit having the following Formula I, Formula II, or both:

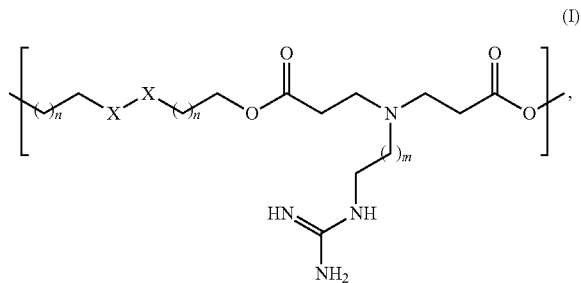

-continued

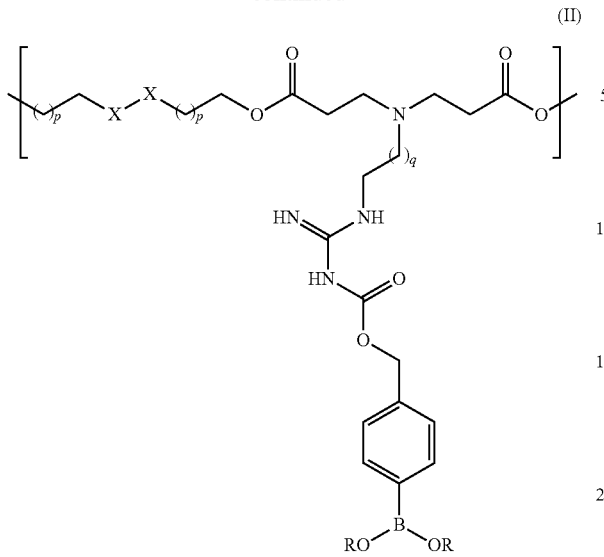

(II)

wherein
each n is independently 1, 2, 3, 4, 5, or 6;
each m is 1, 2, or 3; and
each R is independently H or a polysaccharide selected from the group consisting of dextran, mannan, fucoidan, heparin and a combination of any two or more of dextran, mannan, fucoidan, and heparin.

2. The nanoparticle of claim 1, wherein each R is independently H or dextran.

3. The nanoparticle of claim 1, wherein each n is 1.

4. The nanoparticle of claim 1, wherein each m is 1.

5. The nanoparticle of claim 1, wherein the biodegradable polymer has a weight average molecular weight of 1 kD to 40 kD.

6. The nanoparticle of claim 1, wherein the one or more polysaccharides are selected from the group consisting of dextran, mannan, fucoidan, heparin and a combination of any two or more of dextran, mannan, fucoidan, and heparin.

7. The nanoparticle of claim 1, wherein the one or more polysaccharides are dextran.

8. The nanoparticle of claim 1, wherein the one or more polysaccharides have a weight average molecular weight of 3 kD to 300 kD.

9. The nanoparticle of claim 1, wherein the antibacterial drug is one or more of rifampicin, gentamycin, streptomycin, clindamycin, tetracycline, erythromycin, ciprofloxacin, sulfathiazole, spectinomycin, roxithromycin, sisomicin, novobiocin, isoniazide, clarithromycin, salinomycin, or roxithromycin.

10. A pharmaceutical composition comprising a nanoparticle of claim 1 and a pharmaceutically acceptable carrier or excipient.

11. A method of treatment comprising administering to a subject suffering from a bacterial infection an effective amount of a nanoparticle of claim 1.

* * * * *